United States Patent [19]

Monji et al.

[11] 4,323,647

[45] Apr. 6, 1982

[54] STERIC HINDRANCE ENZYME IMMUNOASSAY

[75] Inventors: Nobuo Monji, Miami Springs; Albert Castro, Miami, both of Fla.

[73] Assignee: University of Miami, Coral Gables, Fla.

[21] Appl. No.: 197,063

[22] Filed: Oct. 15, 1980

[51] Int. Cl.³ .................. G01W 33/54; C12W 9/96
[52] U.S. Cl. .................................. 435/7; 23/230 B; 424/8; 424/12; 435/188; 435/810
[58] Field of Search .......... 435/5, 7, 184, 188, 435/810, 813; 424/12; 23/230 B

[56] References Cited

U.S. PATENT DOCUMENTS

| | | | |
|---|---|---|---|
| Re. 29169 | 4/1977 | Schuurs et al. | 435/7 |
| 3,654,090 | 4/1972 | Schuurs et al. | 435/7 |
| 3,666,421 | 5/1972 | Price | 422/57 |
| 3,791,932 | 2/1974 | Schuurs et al. | 435/7 |
| 3,839,153 | 10/1974 | Schuurs et al. | 435/7 |
| 3,850,752 | 11/1974 | Schuurs et al. | 435/7 |
| 3,852,157 | 12/1974 | Rubenstein et al. | 435/7 |
| 3,875,011 | 4/1975 | Rubenstein et al. | 435/7 |
| 3,879,262 | 4/1975 | Schuurs et al. | 435/7 |
| 3,880,715 | 4/1975 | Schneider | 435/7 |
| 3,905,871 | 9/1975 | Rubenstein et al. | 435/7 |
| 3,935,074 | 1/1976 | Rubenstein et al. | 435/7 |
| 4,016,043 | 4/1977 | Schuurs et al. | 435/7 |
| 4,190,496 | 2/1980 | Rubenstein et al. | 435/7 |
| 4,203,802 | 5/1980 | Rubenstein et al. | 435/7 |
| 4,213,764 | 7/1980 | O'Connor | 23/230 B |
| 4,233,401 | 11/1980 | Yoshida et al. | 435/810 |
| 4,273,866 | 6/1981 | Voss et al. | 435/7 |
| 4,279,992 | 7/1981 | Bougaslaski et al. | 435/7 |

OTHER PUBLICATIONS

Monji, et al., "Steric Hindrance Enzyme Immunoassay (SHEIA), A Novel Method in Enzyme Immunoassay", *Res. Comm. Chem. Path. Pharm*, vol. 26, No. 1, (1979), pp. 187–196.

Steers et al., "B–Galactosidase", *Methods of Enzymology*, vol. XXXIV Part B, Academic Press, N.Y. (1974), pp. 350–358.

Daughaday et al., "Methods of Separating Antibody-Bound From Free Antigen", *Principles of Competitive Protein-Binding Assays*, Odell et al., ed., J. B. Lippincott Co., Philadelphia, pp. 303–324.

Castro, et al., "Automated Radio Immunoassay of Choriomammotropin (Human Placental Lactogen)", *Clin. Chem.* vol. 22, No. 10, (1976) pp. 1655–1658.

Wisdom "Enzyme-Immunoassay", Clinical Chem. 22, 1243–1255 (1976).

Skelley, "Radioimmunoassay", Clinical Chem. 19, 146–186, (1973).

Schuurs et al., Clinical Chem. Acta 81, 1–40 (1977).

Ratcliff, "Separation Techniques in Saturation Analysis", Br. Med. Bull. 30, 32–37 (1974).

Dray et al., Biochem. Biophys. Acta. 403, 131–138 (1975).

McEwen et al., Nature 226, 263 (1970).

Vonderbaar et al., Biochem. Biophys. Acta. 176, 626 (1969).

Exley et al., FEBS Letters 79, 301–304 (1977).

Dittmar et al., Clinical Chem. 25, 227–229 (1979).

Kitagawa and Aikawa, J. Biochem. 79, 233–236 (1976).

Murphy et al., J. Clin. Endocr. 28, 343 (1968).

Murphy et al., J. Clin. Endocr. 27, 973 (1967).

Murphy et al., J. Clin. Endocr. 24, 187 (1964).

Steers et al., Methods in Enzymology 34, 350–358 (1974).

FEBS Letters 91, 162–165 (1978).

Nature 219, 168 (1968).

Page et al., J. Clin. Endocr. 28, 200 (1969).

Exley et al., Steriods 18, 593 (1971).

Rubenstein et al., "Homogenous Enzyme Immunoassay a New Immunochemical Technique", Biochem. Biophys. Research Comm. 47, 846–851 (1972).

Yalow and Berson, J. Clin. Invest. 39, 1157 (1960).

*Primary Examiner*—Thomas Wiseman
*Attorney, Agent, or Firm*—Irons and Sears

[57] ABSTRACT

A novel separation technique is described that is particularly useful for effecting separations in enzyme immunoassay procedures. A mixture, in an aqueous liquid vehicle, of (1), ligand-enzyme conjugate, and of (2), the conjugate bound through its ligand moiety to a receptor, is brought into contact with an insoluble, immobilized pseudo-substrate material, to which the enzyme normally binds. Free conjugate binds and becomes insoluble. Bound conjugate remains in the liquid phase. The ligand may be an antigen and the receptor, the antibody to the antigen.

This separation technique makes feasible several sensitive immunoassay procedures. The material to be assayed may be, for example, rubella virus; hepatitis B surface antigen; gonorrhea antigen; the antibody to any of the foregoing; a general antibody, i.e., an immunoglobulin; a hormone such as choriomammotropin; a steroid, hapten, or the like.

52 Claims, 9 Drawing Figures

STERIC HINDRANCE ENZYME IMMUNOASSAY

BACKGROUND OF THE INVENTION

1. Field of the Invention

This invention relates specifically to a new assay procedure for the detection and measurement of certain biologically active substances, particularly immunochemical substances. This new assay procedure permits rapid qualitative and quantitative determinations to be made in an advantageous manner. The invention also relates to a novel separation technique that is of general utility, and more particularly, to kits useful for assay procedures.

2. Statement of the Prior Art and Other Information

There is a continuing need for rapid, accurate qualitative and quantitative determinations of many kinds of biologically active substances at extremely low concentrations, i.e., at physiological concentrations.

Today, there is for example a need for determining the presence of drugs or narcotics in body fluids, such as saliva, blood or urine. In addition, in medical diagnosis, it is frequently important to be able to detect and quantify the presence of various substances which are synthesized naturally by the body or ingested. These include hormones, both steroidal and polypeptides, prostaglandins, and toxins, as well as other materials which may be involved in body functions. Frequently, there is concern with extremely small amounts and occasionally, with very small differences in concentrations.

Beside these materials, assays effective at extremely low concentrations would be desirable for a variety of pesticides, such as insecticides, bactericides, fungicides, etc., as well as organic pollutants of other kinds, both in the air and water.

Various methods have been developed in the last two or three decades for the determination of a variety of immunochemical substances, including antigens, antibodies, haptens, and certain low molecular weight substances. Excellent surveys of the field are reported by: Skelley et al., Radioimmunoassay, Clinical Chemistry 19: 146-186 (1973); Wisdom, Enzyme-Immunoassay, Clinical Chemistry 22: 1243-1255 (1976); and Schuurs et al., Clin. Chem. Acta 81: 1-40 (1977). There is also a good description of assay techniques in U.S. Pat. No. 4,213,764, issued July 22, 1980.

Examples of some of the assay methods are:
1. Radioassay techniques
   a. Competitive protein binding assays
   b. Radioimmunoassay (RIA)
   c. Immunoradiometric assays
   d. Sandwich or 2-site immunoradiometric assays
2. Fluoroimmunoassays (FIA)
3. Enzyme immunoassay (EIA)
4. Latex-particle agglutination (LPA)
5. Charcoal-particle agglutination (CPA)
6. Hemagglutination and Hemagglutination Inhibition Assays (HA), (HIA)
7. Radial Immunodiffusion and Double diffusion (RID)
8. Viroimmunoassay (VIA); and
9. Spin immunoassay (SIA), among others.

Many of the immunochemical assay systems involve the use of labels. There are many types of labels that are useful for the detection and measurement of biologically important or interesting compounds or substances in serum or other media.

The administration of most of these tests is hampered by one or more of the following limitations: (1) lack of sensitivity, (2) complexity of the test procedure, (3) instability of reagents, (4) hazardous nature of one or more reagents, (5) impure reagents, and (6) expensive equipment required to perform quantitative and qualitative analysis of the amount of label involved, as in an immunochemical reaction. For a review of the development and evaluation of immunological methods and their uses as diagnostic tools, reference is made to "Immunology as a Laboratory Tool" by Franz Peetoome American Journal of Technology 37: 445-469 (1971).

In addition to the general limitations mentioned above, it should be pointed out that the limitation as to "lack of sensitivity" is a very broad term. Some assay procedures have an acceptable sensitivity within one molecular weight range, but unacceptable sensitivity outside that range. Generally the previously available EIA assay techniques could be selected to provide acceptable sensitivity below 1,500 daltons (homo-geneous EIA) and above 60,000 daltons (heterogeneous EIA), but have not provided fully acceptable sensitivity for antigens, for example, having molecular weights between these two figures.

Both labeled and unlabeled immunochemical assay techniques may employ various devices to separate (1), immunochemical constituents which have reacted, from (2), nonreacted immunochemical constituents, and from (3), substances irrelevant to the test. An excellent survey of separation techniques, Separation Techniques in Saturation Analysis, by J. G. Ratcliff, appears at Br. Med. Bull. 30: 32-37 (1974).

For example, some patented EIA techniques require separation through the use of one component in the antigen-antibody reaction in an "insolubilized" phase for separation; see Schuurs and coworkers, in U.S. Pat. Nos. 3,654,090; 3,791,932; 3,850,752; 3,839,153; 3,879,262; 4,016,043 and Reissue 29,169; see also Ratcliff, supra, at pp. 35-36. The separation of bound and unbound antigen is a critical step in some radioimmunoassay (RIA) techniques as well as in some enzyme immunoassay (EIA) techniques. Marsden, Lab. Management, March: 31-34 (1977). Ratcliffe, supra. Odell et al., Proceedings of the Fifth Tenovus Workshop, Wales, U.K. pp. 207-222 (1975). Collins et al., Proceedings of the Fifth Tenovus Workshop, Wales, U.K. p. 223-225 (1975).

The most widely used separation method in RIA for small antigens is an adsorption technique. This system precipitates antibody unbound tracer using adsorbent materials, such as dextran coated charcoal, talc, or resins, and has advantages in its simplicity and reproducibility.

EIA techniques so far developed, however, rely mainly on the double antibody precipitation method. The double antibody method involves precipitation of antibody-bound enzyme-antigen conjugate using a second antibody produced against the immunoglobulin of the first animal. It is a most reliable and reproducible method. The double antibody method is described by Exley et al. in FEBS Letters 79 301-304 (1977) and FEBS Letters 91 162-165 (1978), and in Ratcliffe, supra, pp. 34-35. This method, however, often requires a long incubation time, frequent washings of the precipitates, and involves complex reaction kinetics. The double antibody technique was probably developed because it is so difficult to find suitable materials that will precipitate only unbound conjugate (i.e., enzyme-antigen, enzyme-hapten, or other enzyme-ligand conjugate); see Wisdom, supra, and Schuurs et al., supra.

Those assay techniques that require the presence of a solid phase, as for effecting separation, are commonly referred to as heterogeneous. Generally assays of this type are considered to have good sensitivity for antigens, other substances having high molecular weights, and like ligands. However such assays are not readily susceptible to automation, because of the need for centrifugation, or other separation step, to separate the solid and liquid phases, and because of the need for repeated washings. In a different assay technique referred to as the homogeneous technique, all of the materials remain in the liquid phase; no solid phase is used. This type of assay is generally considered to have good speed and good sensitivity, but not for antigens and other substances having high molecular weight. The homogeneous type of assay is generally limited as to the molecular weights of the ligands with which it is useful. Most types of homogeneous assay are considered to be useful with ligands of 1,500 daltons molecular weight (M.W.) or less. Moreover, homogeneous assays have been most successfully applied only above the nanogram/ml. level. They are easily adapted to automated clinical equipment and when so adapted, can have high sample processing capability (high throughput).

The homogeneous type of assay method does not require separation of free and bound label but rather depends on the inhibition or activation of the enzyme label by antibody binding (e.g., the EMIT R-type of Syva Corporation of Palo Alto, Calif., for EIA and FRAT, or "free radical assay technique", for SIA). Such assay techniques are described in U.S. Pat. Nos. 3,880,715; 3,852,157; 3,875,011; 3,935,074; and 3,905,871, and in an article by Kenneth S. Rubenstein et al., Homogeneous Enzyme Immunoassay, a New Immunochemical Technique, Biochemical and Biophysical Research Communications 47: 846–851 (1972). Other homogeneous assays having similar but not identical properties to EMIT and FRAT are also known. Unfortunately, homogeneous assays or other currently available similar assays, where the antibody modulates enzyme activity in the assay, suffer from the disadvantage that they are insensitive and unable to measure analytes of more than about 1,500 daltons.

The competitions assay, often used in RIA techniques, is now considered a classical and well known technique for detecting immunochemicals such as antigens at a very low concentrations. It is based upon the competition between labeled and unlabeled antigen for a fixed, limited amount of antibody. As applied to RIA, it is described by R. Yalow and S. Berson in J. Clin. Invest. 39: 1157 (1960). The amount of unlabeled antigen influences the distribution of the labeled antigen between antibody-bound (B) labeled antigen and antibody-free (F) labeled antigen. Generally, the greater the amount of unlabeled antigen that is present, the smaller the amount of labeled antigen that is able to combine with the antibody. In order to obtain conclusive results from the distribution, a good separation between B and F must be made. Methods used for this purpose include, for instance, chromatoelectrophoresis, as described by S. Berson and R. Yalow in The Hormones, edited by G. Pincus et al., Academic Press, New York (1964), vol IV, 557, or insolubilization of the antibodies. This insolubilization can be achieved by chemical means (crosslinking or covalent binding to an insoluble carrier) or by physical methods (adsorption to an insoluble carrier).

Of the limitations cited above, a most serious limitation, as reported in U.S. Pat. No. 4,213,764, has been lack of adequate sensitivity to detect some antigens. In general, three levels of sensitivity are recognizable. Low sensitivity techniques, where materials detected and measured exist in microgram/milliliter quantities, include RID, CPA, and LPA. Intermediate sensitivity techniques, where microgram/milliliter to nanogram/milliliter quantities of materials may be measured, include HIA, HA, FIA, SIA, VIA, and EIA. Until recently only RIA was able to measure with ultrasensitivity the picogram/milliliter to femtogram/milliliter region.

A great many of the techniques listed above require that some form of physically or chemically identifiable label be attached to one or more of the reagents in the assay system in order that the result of a test can be detected. RIA, FIA, EIA, VIA, and SIA all fall into this category. Radioactivity, fluorescent moieties, enzymes, complement, viruses, and electron spin labels are used respectively to generate some form of endpoint signal. The sensitivity with which these labels can be detected directly and fundamentally affects the useful ranges of the test systems using them.

The sensitivity with which a labeling moiety can be measured depends upon the nature of the signal that it generates, the ability to detect that signal, and the intensity of signal available per unit amount of marker molecule, i.e., its specific activity. The radioimmunoassay (RIA) method in its various forms has been recognized as a very sensitive system. The RIA method, unfortunately, has several serious, well recognized disadvantages. The possibility of replacing the radioactive label with an enzyme label was proposed in 1968 by L. E. M. Miles and C. N. Hales; see "Labelled Antibodies and Immunological Assay Systems", Lancet, II, 492 (1968), and Nature 219, 168 (1968).

Since then the EIA technique has been extensively investigated and developed. It is recognized as a potentially extremely sensitive technique, because of the inherent amplification potential of the enzyme label. That is, one molecule of enzyme can convert many molecules of its substrate, to generate the desired signal. Often the signal is a color development.

Among the patents that are representative of the state of the art in the detection and measurement of immunochemical substances by the use of an enzyme label are U.S. Pat. Nos. 3,654,090, 3,666,421, 3,791,932, 3,839,153, 3,850,752, 3,879,262, and 4,190,496.

Each patent and literature item cited in this application is incorporated herein by reference.

The Problem

From the foregoing remarks, it can be seen that there are recognized deficiencies or disadvantages to each type of immunoassay procedure. In fact, there is a very well recognized need in the art, of long standing, for an immunoassay that is sensitive and accurate for the detection and/or determination of ligands of any molecular weight, but especially in the range from about 150 daltons to about 150,000 daltons. The need particularly exists for such an assay that can be automated effectively.

This need is particularly acute with respect to ligands in the molecular weight range from about 1,000 daltons to about 40,000 daltons, where the automation of sensitive and accurate immunoassay procedures has either been very difficult or impossible in the past.

Definitions

Antibody: usually a gamma globulin or immunoglobulin that will react specifically (that is, in an immunochemical reaction) with an antigen or hapten.

Antigen: a substance that can induce the formation of an antibody in vivo, and that is capable of an immunochemical reaction with that antibody.

Double-Antibody: a separation technique which makes use of a second antibody produced against the immunoglobulin of a first animal, to precipitate an immune complex of an antigen and an antibody.

Enzyme: generally a proteinaceous material, that acts as a catalyst, often for a single specific reaction. Sometimes enzymes will catalyze more than one reaction.

Hapten: an incomplete or fragmentary antigen, which must be coupled to a carrier to form an antigen.

Heterogeneous: an immunoassay system in which a solid phase is employed, usually in the separation step.

Homogenous: an immunoassay system in which all of the reactants and the reaction products remain in solution. The detection step is made on the solution.

Homologous: a system in which the same animal or species is used to produce a labeled antigen, the unlabeled antigen, and the antibody.

Heterologous: a system in which the labeled antigen, the unlabeled antigen, and the antibody are produced, respectively, in two or more animal species.

Inhibitor: a substance that modifies the activity of an enzyme, by increasing or decreasing it. It is customary to distinguish two broad class of inhibitors, competitive and noncompetitive, depending on whether the inhibition is or is not relieved by increasing concentrations of substrate. In practice, many inhibitors do not exhibit the idealized properties of purely competitive or purely noncompetitive inhibition. An alternate way to classify inhibitors is by their state of action. Some bind to the enzyme at the same place or side as does the substrate (the catalytic or active site), while others bind at some region (the allosteric site) other than the substrate site. The term inhibitor is use herein to refer to a substance to which the enzyme binds (if the enzyme is not inhibited or hindered as hereinafter described).

Ligand: the particular molecule to be assayed, or one immunochemically equivalent to it. More generally the term refers to the smaller molecule in a complex or conjugate in which the smaller molecule is bound to a larger molecule or substance.

Ligand analog: an analog of the ligand molecule that can be bound to an enzyme and that binds to its specific receptor molecule in substantially the same way as does the ligand. The term "ligand" as used herein is intended to embrace ligand analogs and immunochemically equivalent materials.

Pseudo-substrate: a material to which enzyme binds. In the present invention, the preferred pseudo-substrate material is what usually would be regarded as a competitive inhibitor, when beta-galactosidase is used as the enzyme.

Receptor: a specific binding partner of the ligand (or ligand analog) that is bound to the enzyme. Most often the receptor is a substance such as an antibody that binds specifically to another antigenic substance used herein as a ligand.

Sensitivity: the sensitivity of an assay refers to the lowest quantity of the ligand (immunoreactant, hapten, or other substance) that can be reliably detected by the assay.

Specificity: the degree of freedom from interfering substances.

The Prior Art

The present invention is built upon the extensive background described above. However, it makes available a powerful assay tool that is entirely novel.

One of the important features of the present invention is the use of an insoluble immobilized pseudo-substrate which may be in the form of an affinity gel. In one preferred embodiment of the invention, this immobilized pseudo-substrate has been designed for use in connection with a particular enzyme, beta-galactosidase. The response of that enzyme to several different affinity gels is described in an article by Steers et al., in Methods in Enzymology 34: 350-358 (1974).

Steers et al. formed several different affinity gels, each made from agarose coupled to one of several different inhibitors for the enzyme. Some of these gels, when formed into columns, permitted a solution of the enzyme to flow completely through without inhibition, others exhibited some retardation of enzyme flow, and still others retained the enzyme.

The present inventors and three of their colleagues were seeking to develop an improved assay for determining choriomammotropin (human placental lactogen or HPL) in serum. As a result of their efforts, a competition assay was developed. This assay is described in the publication entitled Enzyme-Linked Immunosorbent Choriomammotropin Assay in Clinical Chemistry 25: 227-229 (1979). In the assay as described in that article, unlabeled hormone competes, with a conjugate of the hormone with beta-galactosidase, for antibody that is bound to polystyrene tubes. The entire assay can be performed in 2½ hours with good precision. The maximum sensitivity of this assay was 200 ug/L. The assay made use of a solid phase anti-choriomammotropin antibody. In the assay procedure, any immunoreaction that occurred caused the hormone or hormone-enzyme conjugate to bind to the solid phase antibody and thus become insoluble. A curve was drawn, in FIG. 1 of the article, to demonstrate proportional displacement of conjugate by unlabeled hormone.

The inventors themselves published a brief description of some aspects of the present immunoassay technology in an article entitled, Steric Hindrance Enzyme Immunoassay, in Research Communications in Chemical Pathology and Pharmacology 26: 187-196 (published on or after Oct. 18, 1979).

BRIEF DESCRIPTION OF THE DRAWINGS

FIG. 1 is a series of five equations in diagrammatic form, intended to illustrate the principles behind and the steps involved in the assay procedure of the present invention, with respect to one embodiment thereof:

SUMMARY OF THE INVENTION

1. The Separation Process

Figure 1A:
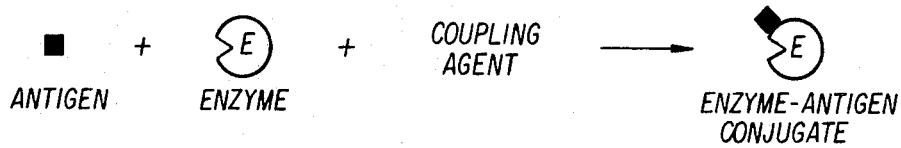
FIG. 1A represents symbolically the formation of enzyme-antigen conjugate through the reaction of antigen and enzyme with a coupling agent.
Figure 1B:
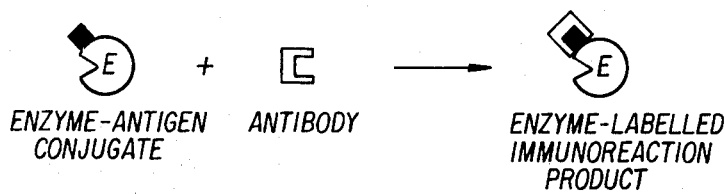
FIG. 1B illustrates the reaction of such a conjugate with antibody to the antigen, to form an immunoreaction product consisting of antibody-bound enzyme-antigen conjugate
Figure 1C:
FIG. 1C illustrates the reaction between solid phase affinity gel (insoluble immobilized pseudo-substrate) and liquid phase enzyme-antigen conjugate, which bind together as the enzyme moiety of the conjugate binds to the pseudo-substrate to remove the conjugate from the liquid phase and place it in the solid phase.
Figure 1D:
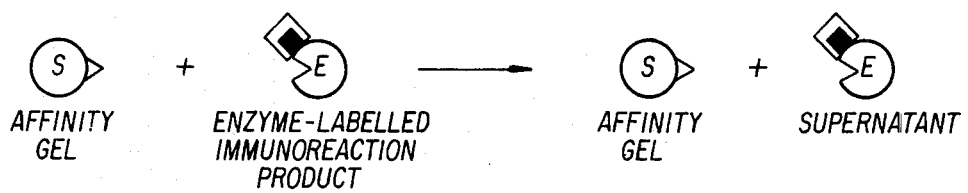
FIG. 1D illutrates in figurative fashion one way in which the presence of the antibody moiety in the antibody-bound enzyme-antigen conjugate prevents binding to the affinity gel, the diagram indicating that such inhibition or interference occurs by reason of steric hindrance, with the enzyme-labeled immunoreaction product remaining, as indicated, in the supernatant liquid after being in contact with the affinity gel.

One important feature of the assay technique of the invention is a separation process. This separation process is effective for separating a ligand-enzyme conjugate from that conjugate that is bound to a receptor for the ligand.

The separation process involves placing in contact (1), a solution containing the ligand-enzyme conjugate and that conjugate bound through its ligand moiety to a receptor for the ligand, and (2), an insoluble immobilized pseudo-substrate for the enzyme. The enzyme, receptor and pseudo-substrate are specially selected materials. The pseudo-substrate is selected so that the free enzyme, and the enzyme moiety of the ligand-enzyme conjugate, bind to the immobilized pseudo-substrate. In addition, the receptor, when bound to the ligand-enzyme conjugate through its ligand moiety, must be one that inhibits the binding of the enzyme of the conjugate to the immobilized pseudo-substrate, as by steric hindrance.

When this separation process is practiced, the ligand-enzyme conjugate is bound and immobilized to the immobilized pseudo-substrate. However, the complex of the receptor to the ligand-enzyme conjugate remains in solution. Consequently, by detecting the enzyme activity of either the supernatant solution, or of the immobilized solid phase, or both, as compared to the original enzyme activity of the conjugate, an assay technique is made possible.

2. Competitive Assay for the Detection/Determination of Ligand Such as an Antigen In a preferred embodiment of the invention, the assay technique is employed for the detection and/or determination of a biologically active substance at a physiological concentration. The biologically active substance may be, for example, an antigen, hormone, steroid, hapten, or the like. To practice the assay, serum suspected of containing the antigen, for example, is mixed with a conjugate of that antigen (or its immunochemical equivalent) with an enzyme. This mixture is then incubated with the antibody for the antigen. After a suitable period of incubation, the mixture is brought into contact with an immobilized pseudo-substrate for the enzyme. In one preferred embodiment the immobilized pseudo-substrate is in a form in which the solution containing the unknown can be passed through it in column form. However, discrete granules of the immobilized pseudo-substrate are also convenient for use, particularly if they are large enough and heavy enough to separate easily from liquid in which they are mixed.

With properly selected reactants according to the present invention, the antigen-enzyme conjugate binds to the immobilized pseudo-substrate and becomes itself immobilized. However, the complex of antibody bound to the antigen-enzyme conjugate (the complex being the immunochemical reaction product of antibody with the antigen moiety of the antigen-enzyme conjugate) is inhibited, we theorize by steric hindrance, from binding to the immobilized pseudo-substrate. This complex therefore remains in solution. If no antigen is present in the unknown serum, then all of the antigen-enzyme conjugate originally employed will bind to the immobilized pseudo-substrate and in effect will be precipitated out of the system. However, if antigen is present in the serum, then some of the antibody employed will react immunochemically with the antigen in the serum, and there is in effect a competitive assay between the antigen in the serum and the antigen moiety of the antigen-enzyme conjugate. Consequently, the enzyme activity that appears in either the supernatant liquid or in the solid phase can be calibrated to indicate the amount of antigen present in the serum. It is preferred that the enzyme activity be read on the liquid phase, although it is technically feasible to read it on the solid phase.

In practice, a 100% reaction efficiency is very difficult to obtain. Consequently, calibration curves are required to be run on blanks and standardized solutions, against which test results can be compared to generate assay result figures.

In more general terms, and expressed in stepwise fashion, an enzyme immunoassay procedure for the detection or determination of a ligand in a liquid sample according to this preferred embodiment of the invention comprises:

(a) mixing a solution containing the ligand to be detected with a predetermined amount of conjugate comprising an enzyme that is bound to a ligand that is the same as or the immunochemical equivalent of the ligand that is to be detected;

(b) mixing and incubating with the mixture produced from step (a) a predetermined amount of a receptor comprising an immunochemical bending partner for both of said ligands, which predetermined amount of receptor is less than that required for complete immunochemical reaction with the ligand moiety of the conjugate, so that the receptor binds to the ligand moiety of the conjugate but only a fraction of said conjugate is so bound as receptor-bound conjugate;

(c) mixing and incubating with the solution from step (b) an amount of insoluble immobilized pseudo-substrate for the enzyme, which immobilized pseudo-substrate is capable of binding to the enzyme moiety of the conjugate that is not bound to receptor, but is incapable of binding to said receptor-bound conjugate, and which amount of immobilized pseudo-substrate is at least sufficient to bind to all of the enzyme moiety of the conjugate of step (a), to form a solid phase and a liquid phase, and (d) detecting or determining the presence or amount of conjugate in either the liquid phase or the solid phase.

For simply detecting an antigen, the assay procedure is used as a qualitative test. The present of the conjugate is detected through its enzyme activity, as through a color reaction with a chromagenic substrate.

To determine the presence of the ligand in the sample in quantitative fashion, initially a standard curve is constructed in the usual fashion, as hereafter described in an exemplary way. The observed value of enzyme activity is then read against the curve, in the manner described in the examples below, to produce a value figure based on the standard curve.

3. Direct Assay for the Detection and/or Determination of Antibody

In another preferred embodiment of the invention, the assay procedure is one for detecting and/or determining the presence of a specific antibody in a medium suspected of containing it. The assay technique for detecting an antibody involves bringing together in an aqueous liquid vehicle, to form a mixture, (1), the medium to be tested, and (2), soluble conjugate of an enzyme with an antigen or immunochemical equivalent thereof, that is immunoreactant with said antibody, and then bringing into contact with this mixture an insoluble, immobilized pseudo-substrate for the enzyme, to which pseudo-substrate the enzyme normally bonds. The immobilized pseudo-substrate may be in the form of granules that are simply mixed into the liquid mixture and then physically separated, or they may be in column form, through which the mixture is passed.

In this assay procedure, the antibody is characterized by the ability, when immunochemically bound to the antigen moiety of the conjugate, to inhibit the binding of the enzyme moiety of the conjugate to the immobilized pseudo-substrate. The conjugate is employed in an amount such that there is always, after incubation of said mixture, an excess of the immunochemically reactant moiety of the conjugate over that needed for complete immunochemical reaction with the amount of antibody present.

The next step in this procedure involves separating the insoluble pseudo-substrate from the liquid. The separated insoluble pseudo-substrate has bound to it free conjugate that is not bound to the antibody. The enzyme activity of the remaining liquid is then detected as an indicator of the presence, if any, of the antibody in the initial medium. The detection step could also be applied to the solid phase. In either case, for a quantitative determination of the amount of antibody in the sample, a standard curve is constructed initially, and then the observed value of enzyme activity is read against the standard curve to generate a value for antibody concentration in the sample.

4. Competitive Assay for the Detection and/or Determination of Antibody

In still another preferred embodiment of the invention, the assay procedure is one for detecting the presence of a general antibody in a medium that is suspected of containing it. In this case a mixture is formed in an aqueous liquid vehicle of (1), the medium that is suspected of containing the general antibody; (2), soluble conjugate of said antibody, or the immunochemical equivalent thereof, with an enzyme; and (3), an immunochemical receptor for the general antibody consisting of antiserum to said antibody. The antiserum must be capable of binding to the antibody and to the antibody moiety of the conjugate.

The next step involves bringing into contact this mixture and insoluble immobilized pseudo-substrate for the enzyme, to which pseudo-substrate the enzyme normally binds. The antiserum is characterized by the ability, when bound to the antibody moiety of the conjugate, to inhibit the ability of the enzyme moiety of the conjugate to bind to the immobilized pseudo-substrate. The immobilized material is then separated from the liquid, and the enzyme activity of the liquid is detected as an indicator of the presence, if any, of general antibody in the original medium. As with other competitive assays, this may be made a quantitative assay through the use of a standard curve.

5. General

All of these preferred assay procedures of the invention may be conducted to be either qualitative assays, quantitative assays, or both.

In each of these assay procedures, the amount of immobilized pseudo-substrate employed should be in excess over that needed for complete binding with all of the enzyme of the conjugate. The amount of the excess may be slight, as for a single assay of the batch kind using the immobilized pseudo-substrate in the form of granules, or very substantial, as where it is used in the form of a packed column. For practical reasons, generally a substantial excess will be used.

Also, in each assay procedure, it is technically feasible to make the observation of the result on either the solid phase pseudo-substrate or on the liquid phase that is separated from it. However, observations taken on the liquid phase are simpler and represent the preferred technique.

DETAILED DESCRIPTION OF THE INVENTION

In its broader aspects, the invention is concerned with a separation technique based on the inhibition of enzyme binding to an immobilized pseudo-substrate, as by steric hindrance.

Based upon the use of our novel separation technique, this invention provides a sensitive, automatable method for detecting or determining extremely low concentrations of a wide variety of organic materials, by relating the presence of a particular unknown to enzymatic activity. The assay procedure of the invention is applicable to ligands having a wide spectrum of molecular weights, including for example antigens in the molecular weight range from 150 to about 150,000.

The invention is also concerned with a kit that is useful for those who may wish to practice the assay. The kit includes supplies of those materials needed for use in the assay, at concentrations and in amounts useful in the assay procedure, and printed instructions.

Measurements of the kind permitted by the assay of the invention are valuable in the detection and diagnosis of disease, and also in monitoring the effectiveness of pharmacologic agents and other treatments.

As those in the art understand, an amplification is inherent in the assay since one molecule of enzyme can transform a large number of molecules of substrate. The amplification is achieved by bonding the ligand to be assayed, or its immunological equivalent, such as a ligand analog, to an enzyme. This combination is referred to in the art and herein as a ligand-enzyme conjugate.

The particular molecule to be assayed is referred to herein as a ligand. For some purposes, a ligand analog may be employed in preparing the ligand-enzyme conjugate, as will hereafter be described. A ligand analog will include either a ligand that is modified by replacing a proton with a linking group, to effect covalent coupling to the enzyme, or it may be a ligand or analog that is covalently coupled to the enzyme. A ligand analog is a ligand modified by some means other than simple replacement of a proton that provides a linking site for coupling to the enzyme.

Competitive Assay Procedures for Antigens and the Like

Both the ligand and the ligand moiety of a ligand-enzyme conjugate are capable of binding to specific sites in a receptor molecule. In conducting the assay, reliance is placed on the fact that the ligand and the ligand moiety of the ligand-enzyme conjugate compete for these sites.

Compounds of very similar structures may serve to compete for reactive sites on an immunochemical binding partner, e.g., morphine glucuronide and codeine will compete with enzyme-bound-morphine for binding to certain types of morphine antibodies. In most instances, this is advantageous in permitting one to assay for a class of physiologically closely related compounds, rather than just for a single specific ligand.

Normally, the ligand, ligand-enzyme conjugate and receptor will be soluble in the aqueous ligand medium employed. The substrate(s) for the enzyme may or may not be soluble in the medium. In some situations it may be desirable to provide a synthetic substrate which is not soluble or to employ an insoluble natural substrate.

In carrying out the assay, the unknown solution containing the ligand, which solution may be a serum, is combined with a known quantity of a ligand-enzyme conjugate. Ordinarily buffer is employed in this initial mixture. The receptor is then added to and incubated with this mixture. Generally the quantities of conjugate and of receptor are accurately known and are carefully controlled so that the ligand moiety of the conjugate is present in an approximately 50% immunochemical excess relative to the active sites of the receptor. The enzymatic activity of the resulting solution, after these three substances have been incubated in the solution, is derived from the amount of conjugate originally employed.

For greatest sensitivity in the assay, the amount of ligand (if any) in the unknown being assayed is at least equal to and preferably is many times the immunochemical equivalent of that present in the conjugate. To the extent that such amounts can be predetermined prior to the assay, based upon expectation, a ratio on the order of about 100 to 1 is preferred.

During incubation, the receptor combines immunochemically with any ligand present from the unknown or serum, and in addition, combines with the ligand moiety of the ligand-enzyme conjugate. Because of the proportions employed, all of the receptor becomes bound, but only a part of the ligand available becomes bound. In this system, often, one mole of receptor can be expected to bind with one mole of the ligand-enzyme conjugate. As those skilled in the art will recognize, however, the one-to-one relationship is not the only possible relationship; each immunochemical binding partner may have several potentially reactive binding sites. The ligand in the unknown, if present, will often be present within an expected or known concentration range. If the ligand-enzyme conjugate is employed in a given or known amount, and a given or known, less than immunochemically equivalent amount of receptor is added, then there is a resulting competition for receptor sites between the ligand and the ligand-enzyme conjugate.

The incubated solution is then brought into contact with affinity gel made up of immobilized pseudo-substrate for the enzyme. This may be done by adding discrete granules of the affinity gel to the solution then incubating the mixture in a shake flask. Separation can then be done at an appropriate time by filtration, centrifugation, or the like. If the pseudo-substrate is immobilized to large beads, settling may be adequate to cause separation to occur. However, it is preferred to use a column of the affinity gel, through which the solution is passed. In either case, the amount of pseudo-substrate made available should preferably be in substantial excess over that required for binding with all of the available enzyme.

The immobilized pseudo-substrate is selected so that the enzyme moiety of the free ligand-enzyme conjugate binds to the immobilized pseudo-substrate and is effectively insolubilized or precipitated. The complex of receptor with the ligand-enzyme conjugate, however, is, we believe, sterically hindered by reason of the presence of the receptor moiety in the receptor-enzyme-ligand complex, so that the enzyme moiety of this complex cannot bind to the immobilized pseudo-substrate.

Knowing the amount of receptor added and the amount of initial conjugate present, a measurement of the enzyme activity in either the liquid phase or the solid phase can be used to reflect the amount of ligand present in the serum as an unknown. It is believed that better results are obtained when the measurement is made on the liquid phase.

The concentrations of the reagents, i.e., the enzyme-bound-ligand and the receptor, may be varied widely. Normally, the concentration of receptor (based on active sites) and enzyme-bound-ligand will be from about $10^{-4}$ M to $10^{-14}$ M, more usually from $10^{-6}$ M to $10^{-12}$ M. The lower limit for the concentration of ligand-enzyme conjugate is predicated on the necessary immunochemical excess of ligand moiety, and also upon the minimum amount of enzyme which can be detected. This will vary with different enzymes as well as different detection systems.

The amount of receptor employed is normally calculated based on its available immunochemically reactive sites and will vary with the concentration and amount of ligand-enzyme conjugate, the ratio of ligand to enzyme in the ligand-enzyme conjugate, and the affinity of the receptor for the ligand. The immunochemical equivalents employed of receptor and of ligand-enzyme conjugate are such that the amount of conjugate employed furnishes approximately a 50% immunochemical excess of ligand, at least. The ratio may vary to a degree depending on binding constants and the amount of ligand suspected of being present in the unknown.

Competitive Assay Procedures for General Antibodies

For detecting a general antibody rather than an antigen-type of ligand, the amount of conjugate of the general antibody with enzyme employed with be selected to optimize the sensitivity of the assay in the concentration range of interest. The concentration ratio of antibody-enzyme conjugate to immunochemical receptor for the general antibody will be selected based upon the minimum and maximum values of the general antibody concentration range of interest.

Conjugate Preparation

In preparing the enzyme conjugate, the ratio of the ligand (for a competitive assay, the ligand will be an antigen or the like, or a general antibody of immunochemical equivalent) to the enzyme in the conjugate will depend upon the identities of the two moieties of the conjugate.

In the preferred embodiment of the invention that is illustrated in detail in Example 1, the conjugate is formed by coupling choriomammotropin to beta-galactosidase through a maleimidobenzoyl bridge. Choriomammotropin is a hormone having a molecular weight above 20,000. It is a single polypeptide. The enzyme beta-galactosidase is a large molecule with a molecular weight of about 550,000. It appears to be a tetramer, with a total of about 12 reactive sites per molecule. The enzyme can be underconjugated or overconjugated. It is difficult to determine the exact amount of choriomammotropin and the exact amount of enzyme in reactant solutions, and very difficult to determine their respective proportions in the conjugate that is formed. Consequently, hormone-to-enzyme molar ratios, when described herein, refer to estimated values calculated from the results obtained by Kitagawa and Aikawa, J.Biochem. 79: 233–236 (1976).

If the conjugate is made up so that the enzyme is underconjugated, that is, the molar ratio of hormone to enzyme is less than about 8:1, then less than desired results are obtained in the assay. When the molar ratio is in the range from about 8:1 to 12:1, best results are obtained in the assay procedure. The ratio that is best will be different for each enzyme and ligand (or antibody) pair.

All other things being equal, the greater the number of enzyme molecules per large ligand, the greater the sensitivity of the assay. However, the enzyme molecules may interfere with receptor recognition, affect solubility, and be deleterious in other ways.

Competitive Assay for the Determination of Choriomammotropin

The invention can be illustrated further as applied to a particular ligand. The determination of choriomammotropin (formerly called human placental lactogen, HPL) in serum is useful for monitoring the progress of high risk pregnancies. The number of samples required in this clinical use is such that a more rapid and economical method is needed than those now presently available. See for example the publication of Dittmar et al in Clinical Chemistry 25: 227–229 (1979), and their appended bibliography.

Our inhibited enzyme immunoassay, or steric hindrance enzyme immunoassay (SHEIA), is particularly useful for assays of serum for choriomammotropin (hereafter for convenience, HPL). To perform the assay, the essentials include serum that is to be assayed, HPL-enzyme conjugate, antibody to HPL, the affinity gel, and of course, substrate for enzyme detection.

The HPL-enzyme conjugate is prepared by bonding HPL to beta-galactosidase through a maleimidobenzoyl bridge. The molar ratio employed for the conjugation should be such that the hormone to enzyme ratio in the conjugate is in the range from 8 to 1 to 12 to 1. The molar ratios can be estimated from the results obtained according to Kitagawa and Aikawa, supra. The production and characterization of rabbit anti-HPL antibody are reported in the article by Castro et al., Clinical Chemistry 22: 1655–1658 (1976).

In addition to the reactants that are employed in the assay, insoluble immobilized pseudo-substrate must be prepared for use in the separation step. For this particular assay, it is preferably prepared by immobilizing a pseudo-substrate for the enzyme beta-galactosidase. Thus, in Ex. 1 hereafter, the 6-aminocaproyl derivative of galactosylamine is attached to agarose. (For convenience, this immobilized pseudo-substrate combination of carrier and pseudo-substrate is referred to hereafter as affinity gel.) It is known that this particular enzyme will not bind to a pseudo-substrate unless a bridge of at least 6 carbons is employed to increase the distance between the pseudo-substrate and the agarose carrier backbone, Steers et al., supra. The affinity gel may be used either in the batch method or in an affinity column.

To practice this embodiment of the invention, serum, conjugate, and something substantially less than the theoretical amount (for reaction with the HPL moiety of the conjugate) of antibody to HPL are incubated together. The mixture is then brought into contact with the affinity gel. Free conjugate binds to the affinity gel, and antibody-bound conjugate remains in solution. By developing a standard curve for the assay, and controlling the relative amounts of the several reactants, the enzyme activity of the supernatant liquid can be determined and, using the standard curve, will indicate the amount of the hormone present in the serum sample.

Measurement of the beta-galactosidase activity remaining in the solution may be done by the method of Dray et al., Biochem. Biophys. Acta. 403: 131–138 (1975), using o-nitrophenyl-beta-D-galactopyranoside (ONGP) as the enzyme substrate.

Construction of the Standard Curve

To make up the standard curve, the concentration of receptor and enzyme will be related to the expected range of concentration of the liquid (HPL in the sample) to be assayed. The sample is used directly. If a relatively high concentration of the unknown ligand is expected to be present, then the unknown solution may be diluted so as to provide a convenient concentration. However, in many biological systems of interest, the amount of material being assayed will be relatively small and dilution of the unknown substrate will often not be required.

To prepare the standard curve for the HPL assay, a series of assay procedures is carried out in which all concentrations of reagents are kept constant, except HPL. In this operation, several standard solutions of HPL are prepared and employed, at different concentrations. In this manner, a series of observed values of enzyme activity in the supernatant liquid is generated. These values can be graphically represented in the form of a standard curve, plotting observed values of enzyme activity against the several different, known concentration values of the HPL standard solutions.

This standardized data can then be used when a serum containing an unknown amount of HPL is employed in the assay, and all of the other conditions are those employed for generating the standard curve. The standardized system can be used to determine rapidly, accurately, and efficiently the amount of HPL in the unknown. This same approach is applicable, of course, for assays for other liquids in other unknowns.

In addition to concentration, other parameters must be fixed for developing the standard curve, and then for conducting assays that will make use of the standard curve. This applies for example to the enzyme assay, temperature, and pH.

The manner of assaying for enzyme activity in the solution or supernatant liquid may take a variety of forms, depending on the enzyme and to some degree upon the particular ligand and the medium in which the ligand is obtained. Preferably, spectrophotometric measurements are employed where the product of a substrate for the enzyme absorbs light. However, other observation techniques may be employed including fluorimetry, measurements of luminescence, and the other techniques that are well known in the art.

This assay is generally carried out at room temperature, that is, at about 20° C., but can be carried out over a broad range of temperatures. Generally ambient temperatures of 15° C. to 40° C. are prevalent under most assay conditions and the assay is operative in this range as well as outside of it, although the ambient temperature obviously affects reaction rates.

The pH at which the assay is carried on is generally in the range from about 5 to about 10, more often from pH 6 to pH 9. Useful buffers for achieving a desired pH include phosphate, citrate-phosphate, borate, amine salts, and the like.

Ligands

Turning now to a general consideration of the reagents, any ligand may be employed for which an appropriate receptor may be found having satisfactory specificity for the ligand. The recent literature contains an increasing number of reports of receptors for an increasingly wide variety of biologically active materials. So long as there is an available specific binding partner, the ligand (unknown) to be assayed may be an immunochemical reactant such as an antigen, a specific antibody, a general antibody, or a variety of other materials. Specific compounds for which receptors can be provided range from simple phenyl alkylamines, e.g., amphetamine, to very high molecular weight polymers, e.g., proteins.

Among drug ligands are compounds which act as narcotics, hypnotics, sedatives, analgesics, antipyretics, anaesthetics, psychotogenic drugs, muscle relaxants, nervous system stimulants, anticholinesterase agents, parasympathomimetic agents, sympathomimetic agents, alpha-adrenergic blocking agents, antiadrenergic agents, ganglionic stimulating and blocking agents, neuromuscular agents, histamines, antihistamines, 5-hydroxytryptamine and antagonists, cardiovascular drugs, antiarrhythmic drugs, antihypertensive agents, vasodilator drugs, diuretics, pesticides (fungicides, antihelminthics, insecticides, ectoparasiticides, etc.), antimalarial drugs, antibiotics, antimetabolites, hormones, vitamins, sugars, thyroid and antithyroid drugs, corticosteroids, insulin, oral hypoglycemic drugs, tumor cells, bacterial and viral proteins, toxins, blood proteins, and their metabolites.

Included among such drugs and agents are alkaloids, steroids, polypeptides and proteins, protaglandins, catecholamines, xanthines, arylakylamines, heterocyclics, e.g., thiazines, piperazines, indoles, and thiazoles, amino acids, etc.

Other ligands of interest besides drugs are industrial pollutants, flavoring agents, food additives, e.g., preservatives, and food contaminants.

Generally, the ligands and receptors to be detected by the use of the present invention will be organic compounds whose molecular weights fall in the range of from about 150 to about 150,000 daltons. However, the assay of the present invention is particularly useful for ligands and receptors with molecular weight within the range from about 20,000 to about 50,000 daltons. The ligand or receptor may be a simple organic compound or a compound having one or more recurring groups, referred to for simplicity as polymers. With care, the present invention can be used for the detection of certain blood proteins whose molecular weight generally is in excess of 100,000 daltons.

Ligands may be divided into three different categories based on their biological relationship to the receptor. The first category is antigens, which when introduced into the bloodstream of a vertebrate, result in the formation of antibodies. The second category is haptens, which when bound to an antigenic carrier, and then introduced into the bloodstream of a vertebrate, elicit the formation of antibodies specific for the hapten. The third category of ligands includes those which have naturally occurring receptors in a living organism, where the receptor can be isolated in a form specific for the ligand.

Antigens are for the most part protein or polysaccharide in nature and generally are foreign to the animal into which they are injected.

In the third group of ligands, i.e., those which have naturally occurring receptors, the receptors may be proteins, nucleic acids, such as ribonucleic acid (RNA) or deoxyribonucleic acid (DNA), or membranes associated with cells. Illustrative ligands which have naturally occurring receptors are thyroxine, many steroids, such as the estrogens, cortisone, corticosterone, and estradiol; polypeptides such as insulin and angiotensin, as well as other naturally occurring biologically active compounds. See Murphy, et al., J. Clin. Endocr., 24: 187 (1964); Murphy ibid, 27: 973 (1967) ibid, 28: 343 (1968); BBA 176: 626 1969); McEwen, et al., Nature, 226: 263 (1970) Morgan, Diabetes, (1966); Page et al., J. Clin. Endocr. 28: 200 (1969).

The ligands may also be categorized by the chemical families which have become accepted in the literature. In some cases, included in the family for the purpose of this invention, will be those physiomimetic substances which are similar in structure to a part of the naturally occurring structure and either mimic or inhibit the physiological properties of the natural substances. Also, groups of synthetic substances will be included, such as the barbiturates and amphetamines. In addition, any of these compounds may be modified for linking to the enzyme at a site that may cause all biological activity to be destroyed. Other structural modifications may be made for the ease of synthesis or control of the characteristics of the antibody. These modified compounds are referred to as ligand counterfeits.

A general category of ligands of particular interest includes drugs and chemically altered compounds, as well as the metabolities of such compounds. The interest in assaying for drugs varies widely, from determining whether individuals have been taking a specific illicit drug, or have such drug in their possession, to determining what drug has been administered or the concentration of the drug in a specific biological fluid.

The ligand analogs of drugs of interest herein generally have molecular weights in the range from about 150 to 1500. They include for example the opiates such as morphine and heroin, meperidine, and methadone, and epinephrine-like drugs such as amphetamine, narceine, ephedrine and L-dopa.

Polypeptide and protein ligands are of great interest. Polypeptides usually encompass from about 2 to 100 amino acids units (usually less than about 12,000 molecular weight). Larger polypeptides are arbitrarily called proteins. Proteins are usually composed of from 1 to 20 polypeptide chains, called subunits, which are associated by covalent or non-covalent bonds. Subunits are normally of from about 100 to 400 amino acid groups (10,000 to 50,000 molecular weight).

Individual polypeptides and protein subunits will normally have from about 2 to 400, more usually from about 2 to 300 recurring amino acid groups. Usually, the polypeptides and protein subunits of interest will be not more than about 50,000 molecular weight. Because of the wide variety of functional groups which are present in the amino acids and frequently present in the various naturally occurring polypeptides, in making a ligand-enzyme conjugate from such as ligand, the enzyme can be bonded to any convenient functionality of the ligand. Polypeptides of interest are ACTH, oxytocin, luteinizing hormone, insulin, Bence-Jones protein, chlorionic gonadotropin, pituitary gonadotropin, growth hormone, rennin, thyroxine bonding globulin, bradykinin, angiotensin, follicle stimulating hormone, etc.

The invention is also useful in assays for steroids. These compounds have a wide range of functionalities depending on their function in the body. In addition to the steroids, are the steroidmimetic substances, which while not having the basic polycyclic structure of the steroids, do exhibit some of the same physiological effects.

The steroids have been extensively studied and derivatives prepared which have been bonded to antigenic proteins for the preparation of antibodies to the steroids. Illustrative compounds include: 17 beta-estradiol-6-(o-carboxymethyl-oxime)-BSA (Exley et al, Steroids 18: 593 (1971)); testosterone-3-oxime derivative of BSA (Midgley, et al., Acta Endocr. 64 supplement 147, 320 (1970)); and progesterone-3-oxime derivatives of BSA (Midgley, et al. ibid.)

These steroids find use as hormones, male and female (sex) hormones, which may be divided into oestrogens, gestogens, androgens, adrenocortical hormones (glucocorticoids), bile acids, cardiotonic glycosides and aglycones, as well as saponins and sapogenins.

Steroid mimetic substances, particularly sex hormones, are illustrated by diethyl stilbestrol. The sex hormones of interest may be divided into two groups; the male hormones (androgens) and the female hormones (oestrogens). Illustrative androgens, with which the invention may be employed, include testosterone, androsterone, isoandrosterone, etiocholanolone, methyltestosterone and dehydroisoandrostone.

Illustrative compounds which may be linked to an enzyme to form an androgen-enzyme conjugate include N-carboxymethoxy testosteroneimine, 17-monotesteroyl carbonate, androsteronyl succinate, testosteronyl maleate, $O^3$-carboxymethyl $O^{17}$-methyl androst-5-ene3-beta,17beta-diol, testosterone 0-carboxypropyl oxime and androsteronyl carbonate.

Illustrative oestrogen compounds which may be detected by the invention include 3-carboxymethyl estradiol, 2-chloromethylestrone estrone glutarate, 0-carboxymethyloximine of 6-ketoestradiol, equilenyl N-carboxymethyl thiocarbamate.

Illustrative gestogen compounds which may be detected include progesterone, pregnenolone, allopregnane-3a:20a-diol and allopregnan-3a-ol-20-one.

Illustrative compounds which may be linked to an enzyme to form a conjugate include 20-progesterone 0-carboxymethyl oxime, 0-carboxymethyl progesterone 3-oxime, pregnenolonyl lactic acid, and allopreganane-3-carboxymethyl-20-ol.

Another important group of steroids is the corticosteroids which includes both the mineral corticoids and the glucocorticoids.

Illustrative compounds of this type which may be bonded to an enzyme to form a conjugate are 17-hydroxydioxycortiocosterone (compound S), deoxycorticosterone, cortisone, corticosterone, 11-dihydrocortisone (Compound F), cortisol, prednisolone and aldosterone.

Illustrative compounds of this type which may be linked to an enzyme to form a conjugate include $O^{21}$carboxymethyl corticosterone, N-carboxymethyl 21-carbamate cortisol, 21-cortisone succinate, 21-deoxocorticosterone succinate, and $O^{17}$-methyl, $O^{21}$-carboxymethyl cortisone.

The assay of the invention is also useful for the detection of antibiotics such as penicillin, chloromycetin, actinomycetin, tetracycline, terramycin, and nucleic acid or derivatives, such as nucleosides and nucleotides. It is also useful for the determination of serotonin, which is 3-(2'-aminoethyl)-5-hydroxyindole.

Enzymes

Enzymes vary widely in their substrates, cofactors, specificity, ubiquitousness, stability to temperature, pH optimum, turnover rate, and the like. Other than interest factors, there are also the practical considerations, that those enzymes selected for use have been characterized extensively, have accurate reproducible assays already developed, and be commercially available.

In addition, for the purpose of this invention the enzymes should either be capable of specific labelling or allow for efficient substitution, so as to be useful in the subject assays. By specific labelling is intended selective labelling at a site in relationship to the active site of the enzyme, so that upon binding of the receptor to the ligand moiety of the conjugate, the enzyme is satisfactorily sterically hindered or otherwise inhibited with respect to the specific immobilized pseudo-substrate that is to be used. When the receptor is bound to the ligand moiety of the conjugate, the degree of substitution should not unreasonably diminish the turnover rate for the enzyme moiety of the conjugate nor substantially change the solubility characteristics of the conjugate.

From the standpoint of operability, a very wide variety of enzymes is available for use. As a practical matter, there are a number of groups of enzymes which are preferred. Employing the International Union of Biochemists (I.U.B.) classification, the oxidorreductases (1.) and the hydrolases (3) are of greatest interest.

Of the oxidoreductases, the ones acting on the CHOH group, the aldehyde or keto group, or the CH-NH$_2$ group as donors (1.1, 1.2, and 1.4 respectively) and those acting on hydrogen peroxide as acceptor (1.11) are preferred. Also, among the oxidoreductases those preferred include those which employ nicotinamide adenine dinucleotide, or its phosphate or cytochrome as an acceptor, namely 1.×0.1 and 1.×0.2, respectively, under the I.U.B. classification.

Of the hydrolases, of particular interest are those acting on glycosyl compounds, particularly glycoside hydrolases, and those acting on ester bonds, both organic and inorganic esters, namely the 3.1 and 3.2 groups respectively, under the I.U.B. classification. Other groups of enzymes which might find use are the transferases, the lyases, and isomerases, and the ligases.

In choosing an enzyme, there are several important criteria. These can be tabulated as follows:

Table 1

Criteria for the Choice of a Preferred Enzyme Label

1. Available cheaply in high purity.
2. High specific activity.
3. Stable under assay and storage conditions.
4. Soluble.
5. Known assay method that is simple, sensitive, rapid, and cheap.
6. Absent from biological fluids.
7. Substrates, inhibitors, and disturbing factors absent from biological fluids.
8. Capable of retaining activity while undergoing appropriate linkage (conjugating) reactions.
9. Capable of being sterically hindered when antibody or other receptor binds to the ligand-enzyme conjugate.
10. Assay conditions compatible with ligand-receptor binding.

In more detail, the enzyme should be stable when stored for a period of at least three months, and preferably at least six months at temperatures which are convenient for storage in the laboratory, normally −20° C. or above.

The enzyme should have a satisfactory turnover rate at or near the pH optimum for binding of the ligand, or of the ligand moiety of the ligand-enzyme conjugate, to the receptor. This is normally at about pH 6-10, usually 6.0 to 8.0. Preferably, the enzyme will have the pH optimum for its turnover rate at or near the pH optimum for binding of the receptor to the ligand.

The enzyme should have a substrate (including cofactors) which has a molecular weight in excess of 300, preferably in excess of 500, there being no upper limit. A product should be either formed or destroyed as a result of the enzyme action on its substrate. The reaction product obtained should be one which absorbs light in the ultraviolet region or the visible region, that is, in the range of about 250-750 nm, preferably 300-600 nm, to facilitate optical or visual detection of enzymic activity.

Preferably, the enzyme which is employed, or other enzymes with like activity, will not be present in the fluid on which the assay is carried out, or if present, can be easily removed or deactivated prior to the addition of the assay reagents. Also, there should not be naturally occurring inhibitors for the enzyme present in fluid to be assayed.

Also, although enzymes of up to 600,000 molecular weight can be employed, usually relatively low molecular weight enzymes will be employed of from 10,000 to 300,000 molecular weight, more usually from about 10,000 to 150,000 molecular weight, and frequently from 10,000 to 100,000 molecular weight. Where an enzyme has a plurality of subunits the molecular weight descriptions refer to the enzyme and not to the subunits.

For synthetic convenience, it is preferable that there be a reasonable number of groups to which the ligand may be covalently coupled or bound, particularly amino groups. However, other groups to which the ligand may be bound include hydroxyl groups, thiols, and activated aromatic rings, e.g., phenolic.

Accordingly, the enzyme selected for use will be one that is already sufficiently characterized so as to assure the availability of sites for linking either in positions which allow for steric hindrance or other form of inhibition of the enzyme when the ligand is bound to the antibody or other receptor, or there should exist a sufficient number of positions as to make this occurrence likely.

The following enzymes are among those often used in EIA, which may have the capability of being used in accordance with the present invention.

TABLE 2

| Enzymes Suitable For Use | |
|---|---|
| Enzyme | Source |
| acetylcholinesterase (EC 4.2.1.1) | — |
| alkaline phosphatase (EC 3.1.3.1) | calf intestinal mucosa and E. coli |
| carbonic anhydrase (EC 4.2.1.1) | Rhizopus nivens |
| beta-D-galactosidase (EC 3.2.1.23) | E. coli |
| glucoamylase (EC 3.2.1.3) | A. oryzae |
| glucose oxidase (EC 1.1.3.4) | fungal |
| glucose-6-phosphate dehydrogenase (EC 1.1.1.49) | Leuconostoc mesenteroides |
| horse-radish peroxidase (EC 1.11.1.7) | horse-radish |
| lysozyme (EC 3.2.1.17) | egg white |
| malate dehydrogenase (EC 1.1.1.37) | pig heart mitochondria |

All of these are available commercially. Many other enzymes that are useful in EIA techniques are identified in U.S. Pat. No. 4,190,496, cols. 32-38.

The Ligand-Enzyme Conjugate

The ligand-enzyme conjugate consists of the ligand covalently linked to one or more enzyme molecules. Such linking can be achieved either by direct condensation or by using external bridging molecules, in accordance with methods known to those skilled in the art.

Thus, the production of enzyme conjugate employing a covalent bond can be effected by difunctional reagents such as carbodiimides, diisocyanates, glutaraldehyde, and bisdiazolbenzidine.

Preferably, the ligand or ligand analog is bonded either directly to the enzyme, by a single or double bond, or to a linking group. For those ligands which are haptens, and for which the receptors are antibodies, the ligand will have been bound to a protein. Since the antibodies will recognize that portion of the ligand molecule which extends from the protein, ordinarily the same linking group will be attached on the same site on the ligand, as was used in bonding the ligand to the protein to provide the antigenic substance.

The functional groups which will be present in the enzyme for linking are amino (including guanidino), hydroxy, carboxy, and mercapto. In addition, activated aromatic groups or imidazole may also serve as a site for linking.

Amino acids having amino groups available for linking include lysine, arginine, and histidine. Amino acids with free hydroxyl groups include serine, hydroxypropyline, tyrosine and threonine. Amino acids which have free carboxyl groups include aspartic acid and glutamic acid.

In most instances, the preferred linking group will be the amino group. Making conjugate from an enzyme requires knowledge of the morphology of the enzyme molecule and, as well, generally some amount of experimentation.

The ligand, of course, may have a great diversity of functionalities. In addition, the functionalities which are present may be modified so as to form a different functionality, e.g., keto to hydroxy, or an olefin to aldehyde or carboxylic acid. To that extent, the choice of groups for linking to the ligand may be varied much more widely than the choice of groups for linking to the enzyme. In both cases, however, a wide variety of different types of functionalities have been developed, specifically for linking various compounds to proteins and particularly to enzymes.

When a cross-linking agent is used in forming the conjugate, the bonds formed must be stable under the conditions of the assay. When bonding the ligand to the enzyme by a cross-linking agent, the enzyme must retain at least a portion of its activity upon isolation. The enzyme must not prevent binding of the ligand to the receptor. The functionalities should permit some selectivity, so that bonding can be directed to specific groups or types of groups in both the ligands and enzymes.

Receptors

The receptor is always a specific binding partner for the ligand in the enzyme conjugate. For the most part, the receptors will be macromolecules which have sites which recognize specific structures. The recognition of the specific structures may be based on van der Waals forces, which provide a specific spatial environment which maximizes the van der Waals forces; diple interactions, either by permanent or induced dipoles; hydrogen and ionic bonding; coordinate covalent bonding; and hydrophobic bonding. For a detailed discussion of such binding mechanisms see Goldstein et al., Principles of Drug Action, Harper and Rowe, New York, 1968.

A macromolecule is generally essential in order that the receptor-ligand-enzyme complex have sufficient bulk or blocking (because of site) contributed by the receptor so that the desired steric hindrance or other form of enzyme inhibition occurs.

The macromolecules of greatest interest are proteins and nucleic acids which are found in cell membranes, blood, and other biological fluids. These compounds include antibodies, ribonucleic acid (RNA) and deoxyribonucleic acid (DNA), and natural receptors.

The most convenient groups of proteins for use in the subject invention are antibodies. These materials are conveniently used in the analysis of the category of ligands referred to as haptens, as well as for antigens. Antibodies are produced by introducing an immunogenic substance into the bloodstream of a living animal. The response to the introduction of the immunogenic substance or antigen is the production of antibodies which act to coat the antigen and detoxify it or precipitate it from solution. The protein forms a coat which is geometrically arranged so as to have the antigen fit the spatial arrangement of the protein. This may be analogised to a lock and key. The interaction is normally reversible, in that the antigen is subject to displacement or removal by various means without destruction of the receptor site of the antibody.

There are many materials which are antigens and will produce an immunogenic response by being introduced into the bloodstream of a vertebrate. However, a number of materials of interest are not antigens, but are haptens, and in that case, an extra step in preparing the antibody is required. This method of preparing antibodies with materials other than antigens is well known, Microbiology, Hoeber Medical Division, Harper and Rowe, 1969. See also, Landsteiner, Specificity of Serological Reactions, Dover Publications, N.Y. 1962; Kabat et al., Experimental Immunochemistry, Charles C. Thomas, Springfield, Ill., 1969; and Williams et al., Methods in Immunology and Immunochemistry, Vol. 1, Academic Press, New York 1967. The material which is to be assayed is bonded to a protein by any convenient means and the modified protein introduced into the blood stream. The same type of bonding groups used with the enzyme attachment to the ligand may be employed.

The antibodies which form will include groups of antibodies which are shaped to fit the foreign moiety (hapten) bonded to the protein. Therefore, antibodies are obtained which are specific to the compound or moiety bonded to the protein. By careful separation techniques, the antibodies primarily concerned with the moiety in question can be concentrated so as to provide an antibody composition which is primarily related to the specific moiety which was bonded to the protein.

To illustrate this method, para-aminobenzene arsonate is diazotized to form the diazo salt. By combining the diazo salt with rabbit globulin, the rabbit globulin may be labeled with para-azobenzene arsonate. By introducing this composition into the blood stream of an animal other than a rabbit, for example a sheep, antibodies can be formed which will have a spatial arrangement which accepts solely the azobenzene arsonate.

In addition to antibodies, there are a number of naturally occurring receptors which are specific to compounds of biological interest. Compounds for which receptors are naturally occurring include thyroxine, corticosterone, cortisone, 11-desoxycortisol, 11-hydroxyprogesterone, estrogen, insulin and antigen. See, for example, Vonderhaar et al., Biochem. Biophysics Acta., 176, 626 (1969). All of these ligands have been studied and reported upon in the literature in connection with studies on their binding with specific receptors.

Immobilized Pseudo-Substrate

The immobilized pseudo-substrate consists, preferably, of two or three components. One of the essential components is an inert carrier. The word "inert" is employed to define the role of the carrier with respect to the assay materials with which it comes in contact, rather than with respect to the pseudo-substrate.

A second component is the pseudo-substrate. In conventional parlance, many of the preferred materials, that can serve as the pseudo-substrate, would be called competitive, reversible inhibitors. For the purposes of the present invention, the pseudo-substrate employed must be one of the type that forms a complex with either free enzyme or with the enzyme moiety of enzyme that is conjugated to ligand. Preferably, but not essentially, the pseudo-substrate-enzyme complex that forms is reversible, so that after the complex has formed and has served its purpose, the complex can be uncoupled and the enzyme released, to permit eventual reuse of the immobilized pseudo-substrate.

These are the two essential components of the immobilized pseudo-substrate, that is, the carrier and the pseudo-substrate itself. In some cases, the pseudo-substrate may be immobilized directly to the carrier. However, preferably, a third component is present in the form of a covalent coupler, that chemically couples the pseudo-substrate to the carrier.

A most important property of the immobilized pseudo-substrate is its ability to form a complex with enzyme, so that free enzyme-ligand conjugate is bound to the immobilized pseudo-substrate to effect a separation for assay purposes. The manner in which the immobilized pseudo-substrate is prepared will depend upon the identity of the enzyme that is to form the complex. Those skilled in enzymology are sensitive to the spatial requirements that will permit the enzyme-pseudo-substrate complex to form. See for example, Steers et al., Methods in Enzymology, supra, where several different types of affinity gel are described, some of which were effective in forming complexes and some which were not. The authors concluded that the enzyme (beta-galactosidase) with which they were working required that the pseudo-substrate be connected to the particular carrier, that they were using, by a cross-linking molecule containing at least a certain minimum number (6) of carbon atoms, to permit the enzyme-pseudo-substrate complex to be formed.

The carrier may be either organic or inorganic. In either case, it is preferably in the form of particles that remain discrete whether used by admixture with the assay liquid, or packed in a column through which the assay liquid is passed. Generally the same techniques that are employed for immobilizing enzymes are useful for immobilizing pseudo-subtrate, subject to the qualification that the bridge must be one that permits the complex to form between the immobilized pseudo-substrate and the free conjugate. Thus the carrier may be in the form of alumina granules, polystyrene beads, porous glass beads, charcoal granules, glass fibers, and the like. Similarly, organic carriers such as Sephadex and agarose are useful.

In one preferred form of immobilized pseudo-substrate, agarose-aminocaproyl-beta-D-galactosylamine is employed as a solid phase enzyme affinity complex.

Enzyme Assay

Turning now to a consideration of the determination of the amount of active enzyme, assaying for enzymatic activity is well established for a wide variety of enzymes. A wide diversity of media, conditions and substrates have been determined for measuring enzymatic activity. See, for example, Bergmeyer, Methods for Enzymatic Analysis, Academic Press, New York, 1965. Since there are differences, not only between assays for different enzymes, but even in the variety of assays for a particular enzyme, no general description of the assay techniques is possible, but none is needed for those skilled in the art.

Specific Examples

The invention will now be described further by detailed descriptions of several specific demonstrations of assays conducted in accordance with the invention. In these examples, and elsewhere throughout this application, all references to parts are to parts by weight, and all temperatures are in degrees Celsius, unless specifically stated otherwise.

EXAMPLE 1

Steric Hindrance Enzyme Immunoassay for Choriomammotropin (HPL)

A. Introduction

Figure 1E:
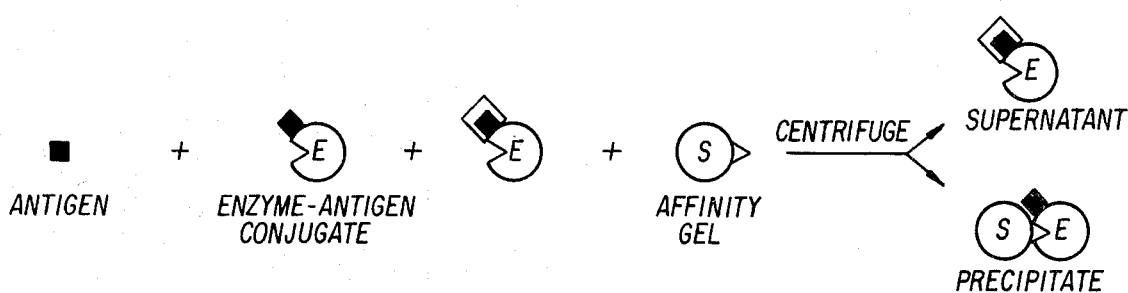
FIG. 1E illustrates what is believed to take place during the actual assay procedure of one preferred embodiment of the invention, where, after incubation, a liquid mixture containing antigen, enzyme-antigen conjugate, and antibody-bound enzyme-antigen conjugate, is brought into contact with affinity gel, the affinity gel being in the form of discrete particles that are incubated with the liquid mixture, then separated by centrifugation, the antibody-bound enzyme-antigen conjugate remaining in the supernatant liquid, and the non-immunochemically reacted enzyme-antigen conjugate being bound to the affinity gel and separated out with it from the liquid.

The theoretical basis for this assay is illustrated in FIGS. 1A–1D inclusive, and these figures are self-explanatory. FIG. 1E is a diagrammatic representation of the assay that was demonstrated in this example, except that the ligand is identified as an "antigen", whereas in this example, it was in fact the hormone, choriomammotropin. For simplicity of illustration and ease of comprehension, FIG. 1E is an over-simplified representation. For example, the reaction mixture would actually contain some antigen-antibody complex, but this is not shown in the drawing, since in essence it plays no active part in the assay because of the use of a standard curve, as explained hereafter.

B. Materials

Commercial materials were used if available. This was the case with the hormone choriomammotropin (HPL), the enzyme beta-galactosidase from $E.$ $coli,$ and certain chemicals whose use is described hereafter: meta-aminobenzoic acid, benzaldehyde, and maleic anhydride.

The rabbit anti-HPL antiserum was prepared and characterized as reported in Castro et al., Clin Chem. 22: 1655–1658 (1976), and following the procedure described there, its affinity constant was calculated to be $3.1 \times 10^9$.

C. Conjugate Preparation

To make the hormone-enzyme conjugate, m-maleimidobenzoyl-N-hydroxysuccinamide (MBS) was first synthesized by the procedure of Kitagawa et al., supra, for use in coupling HPL to the enzyme through a maleimidobenzoyl bridge. 75 $\mu$l of solution of MBS (5 mg/ml, 1.2 moles) in tetrahydrofuran was added to 2 ml phosphate buffer (pH 7.0, 0.05 M, buffer A) containing 15.4 mg of HPL (0.66 moles). The mixture was incubated for 30 minutes at room temperature. One ml of citrate-phosphate buffer (pH 5.0, 1 M) was then added and the precipitate formed was collected by centrifugation at $2,000 \times g$ for 15 minutes. The precipitate was washed twice with 0.01 M citrate buffer (pH 5.3, 2 ml$\times 2$).

The washed precipitate was then redissolved in buffer A. One ml of beta-galactosidase dissolved in buffer A was then added to the HPL-MBS solution and incubated for 2 hours at room temperature. No appreciable reduction in enzyme activity was observed during the incubation. The reaction mixture was then directly chromatographed on a Sephadex G-75 column (1.8×33 cm) using buffer A as the eluting buffer.

The fractions of eluate containing the peak of enzyme activity were further purified by affinity chromatography, to remove overconjugated enzyme and enzyme which had not bound to inhibitor. The enzyme-conjugate solution was passed through a column (1×3 cm) containing agarose-6-aminocaproyl beta-D-galactosylamine (immobilized pseudo-substrate) which had been washed extensively with buffer A. After passing the conjugate solution into the column, the column was again washed extensively with buffer A. When no more enzyme activity was detected in the eluate, the column was eluted with borate buffer (pH 10.0, 0.1 M). The column contents consisted of particles of the immobilized pseudo-substrate to which the hormone-enzyme conjugate was immobilized.

The fractions containing the major peak of enzyme activity were collected and then dialyzed overnight in one liter of buffer A. After dialysis, 0.05% NaN$_3$ and 2 μl/ml of 1 M MgCl$_2$ were added and stored at 4° C. Measurement of beta-galactosidase activity was done by the method of Dray et al., Biochem. Biophys. Acta 403, 131–138 (1975) using o-nitrophenyl-beta-D-galactopyranoside (ONGP) as the enzyme substrate.

To determine the relative amount of enzyme that was conjugated with HPL, the conjugate was mixed with an excess of rabbit anti-HPL antibody. Goat anti-rabbit gamma-globulin (Calbiochem, La Jolla, Calif. 92037) was then added in excess. The resulting precipitate contained more than 90% of the enzyme activity initially present. A control with normal rabbit serum in place of the antibody gave no detectable enzyme activity in the precipitate.

D. Affinity Gel Preparation

One of the best inhibitors for beta-galactosidase isolated from *E. coli* is beta-D-galactosylamine ($K_I=0.225$ mM), Lai, et al., Biophys. Res. Comm. 54: 463–468 (1973). This inhibitor is a potent competitive inhibitor. Agarose attached 6-aminocaproyl derivative of galactosylamine has been used widely in affinity chromatography for the purification of beta-galactosidase from various sources, Harpaz, et al., Biochem. Biophys. Acta. 341: 213–221 (1974).

It is known that beta-galactosidase will not bind to an inhibitor unless a long arm (at least 6 carbon chain) is used to increase the distance between the beta-D-galactosylamine and the agarose back bone, indicating rather strict physicochemical requirement for their bindings, Steers, et al., supra. We utilized the hindrance of this rigid steric requirement by antibody to develop the enzyme immunoassay. We have employed the batch method to separate antibody bound conjugate and unbound or free conjugate in this example.

E. Assay Procedure

To each of an array of glass test tubes (16×10 mm) 150 μl of buffer A was added, followed by addition of 5 μl of each of several standard solutions containing respectively 0, 2, 4, 6 and 10 mg/l of HPL in 5% BSA solution. One hundred μl each of the HPL-enzyme conjugate of a dilution characterized by absorbance of 0.6–0.8 at 420 nm and of 0.5% BSA were then added successively. After mixing, 100 μl of 1:1,000 dilution of anti-serum was added to each tube, which was then incubated for 1 hour at 4° C.

One hundred μl of buffer A containing 5 μl (wet volume) of washed agarose-6-aminocaproyl beta-D-galactosylamine particles (the affinity gel) was then added to each tube. The tubes were then placed in a shaker operated at 100 rpm, for 60 minutes.

Following incubation in the shaker, the test tubes were centrifuged for 10 minutes at 2,000×g and 250 μl of the supernatant liquid was taken from each tube and assayed for enzyme activity, by adding the substrate ONGP and observing the intensity of any color change.

The assay showed a maximum sensitivity of 4 ng/tube. In a standard curve produced from the data generated by the procedure described above, as represented in FIG. 2 of the drawings, the assay system was selected to cover a range of 0–10 mg/l with maximum sensitivity between 0–4 mg/l using the 5 μl sample size.

The observations were as follows:

TABLE 3

Figure 2:
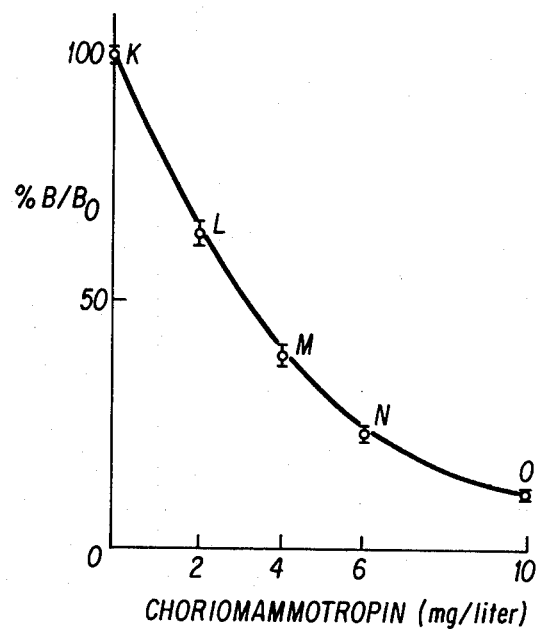
FIG. 2 is a standard curve prepared for use in connection with an assay procedure for detecting the presence in serum of choriomammotropin in accordance with one preferred embodiment of the invention as specifically demonstrated in Example 1 hereof.

| Standardized Solution of HPL Containing, in mg/l | Observation, % B/B$_o$ | Plotted In FIG. 2 as Point |
|---|---|---|
| 0 | 100 | K |
| 2 | 65 | L |
| 4 | 40 | M |
| 6 | 25 | N |
| 10 | 20 | O |

In the center column of the caption in Table 3 above, % B/B$_o$ is a percentage ratio. B is the amount of conjugate that is bound to anti-HPL antibody in the presence of the different respective amounts of the standards, as determined by absorbance at 420 nm. B$_o$ is the value determined by absorbance at 420 nm with the sample to which no HPL was added. Actually, each point plotted in FIG. 2 represents the mean value±S.E. from four replicate runs.

To use the standard curve to make assays on serum containing an unknown but generally suspected amount of HPL, best results are obtained if the unknown contains an amount of HPL that generates a reading on the most sensitive part of the curve, i.e., preferably that portion of the curve falling between points K and M of FIG. 1.

Generally the amount of HPL to be found in a blood sample of an expectant mother can be predicted in a rough way. If necessary the blood sample can be adjusted in concentration by dilution, so that the assay result will fall within the desired section of the standard curve.

As those skilled in the art will understand, other standard curves can be generated by using different concentrations. With each standard curve, however, the assay procedure is the same. The assay is run to establish a B value for the unknown, a % B/B$_o$ value is calculated, and the standard curve is then used to read off a concentration value of HPL for the unknown. Generally such an assay can be completed in 2½–3 hours.

Figure 3:
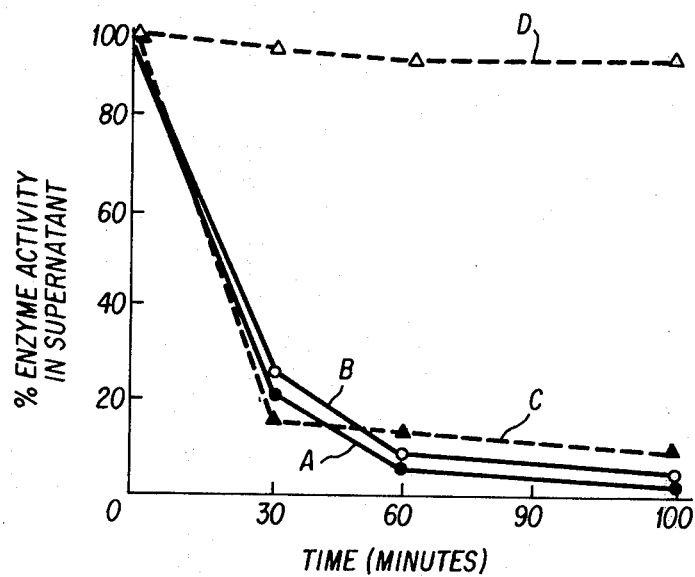
FIG. 3 is a series of plots of data illustrating the effect of incubation time upon the binding of ligand (antigen-)enzyme conjugate to insoluble, immobilized pseudo-substrate, where the conjugate and immobilized pseudo-substrate are essentially those of Ex. 1 hereof.

The effect of incubation time upon the formation of an insoluble complex between the HPL-enzyme conjugate and the affinity gel is illustrated in the several curves in the graph of FIG. 3.

The ratio of HPL to the enzyme was not directly determined. The ratios reported hereafter are the expected values calculated from the results obtained by Kitogawa et al., supra. The conjugates in each case were purified by affinity chromatography prior to use.

In order to precipitate the enzyme from solution, particles of affinity gel were added to the solution and incubated in a shaker (100 rpm) for 30, 60, 90 and 120 minutes. The solid phase was then precipitated by centrifugation, and the enzyme activity in the supernatant was examined. The results showed that only 5% of the added enzyme had become bound to 5 μl (wet volume) per tube of affinity gel with 60 minutes or more of incubation (FIG. 3).

In FIG. 3, Curve A reports the results obtained with a conjugate above, with an expected 2:1 ratio of HPL to enzyme; Curve B, with a conjugate with a 2:1 ratio, incubated for one hour with antibody to HPL prior to the separation step; Curve C, with a conjugate, alone, with an 8:1 ratio, and Curve D, with a conjugate with an 8:1 ratio, incubated for one hour with antibody to HPL, prior to the separation step.

Figure 4:
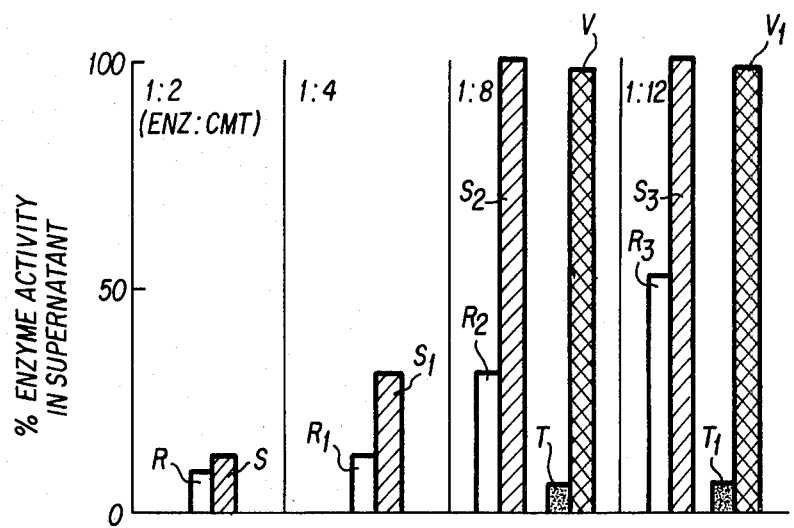
FIG. 4 is a bar chart illustrating the effect of the molar ratio of hormone to enzyme in the conjugate, upon complex formation between the conjugate and the immobilized pseudo-substrate, where the conjugate and immobilized psuedo-substrate are prepared as in Ex. 1 hereof, except for the molar ratios of hormone to enzyme, the abbreviations ENZ and CMT representing beta-galactosidase and choriomammotropin, respectively.
Figure 5:
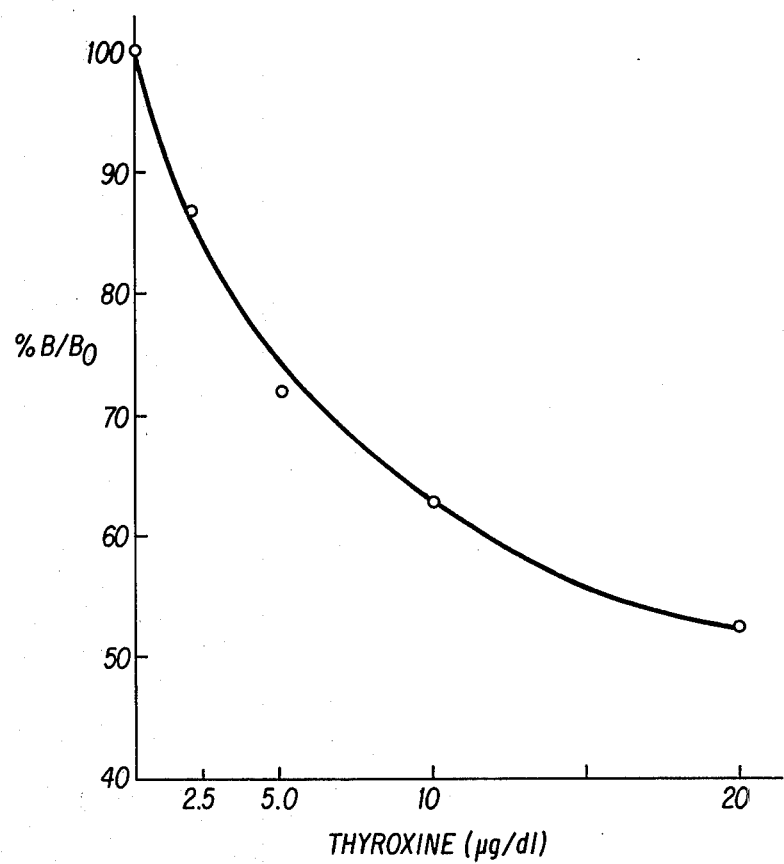
FIG. 5 is a standard curve generated for use in an assay procedure for the protection of thyroxine in serum in accordance with another preferred embodiment of the invention as demonstrated in Example 2 hereof.

Prior to purification of the enzyme conjugate using the affinity column, when the conjugation of HPL to beta-galactosidase was carried out at different molar ratios, the enzyme activity remaining in the supernatant, following incubation with excess affinity gel and centrifugation, was found to depend on the molar ratio employed of enzyme to HPL, in preparing the conjugate. With an expected HPL to enzyme ratio in the conjugate of 8:1 or 12:1, about 30% or 50%, respectively, of the total enzyme activity remained in the supernatant, while a reduction in the expected molar ratio to 4:1 or less resulted in about 10% remaining in the supernatant (FIG. 4). This inhibition of the binding of conjugate to the affinity gel suggested a possible steric hindrance on binding, by the HPL itself. When these conjugates were purified by the affinity column, however, the enzyme activity remaining in the supernatant was reduced to about 5%, suggesting the removal of overconjugated enzyme (FIG. 4).

The effect of the molar ratio of HPL to enzyme, on complex formation with the affinity gel, is illustrated in the bar chart of FIG. 4. Bars R, $R_1$, $R_2$ and $R_3$ illustrate the situations observed in cases where the enzyme conjugate was incubated with the affinity gel without having undergone purification by affinity chromatography. Bars T and $T_1$ illustrate the observations made when the conjugate had been purified by affinity chromatography. Bars S, $S_1$, $S_2$ and $S_3$ illustrate the results observed when the conjugate, without purification by affinity chromatography, was incubated for one hour with antibody to HPL, then with the affinity gel. The readings on enzyme activity in each case were taken on the supernatant liquid, after separation from the affinity gel. Finally, bars V and $V_1$ illustrate observed results where the conjugate was purified by affinity chromatography, then incubated for one hour with antibody to HPL, prior to separation of the supernatant from the affinity gel.

In summary, we have developed, and demonstrated in this example, a new method for the separation of antibody bound and unbound enzyme conjugates. The technique as applied to the assay of choriomammotropin involves the use of beta-D-galactosylamine bound to agarose to separate the unbound choriomammotropin-beta-galactosidase conjugates from antibody bound conjugates. When beta-galactosidase was conjugated with choriomammotropin using the N-hydroxy-succinamide ester of m-maleimidobenzoic acid, the affinity of the enzyme conjugate to beta-D-galactosylamine attached to agarose diminished markedly following incubation with antibody. In a typical enzyme immunoassay of choriomammotropin, as described in this example, 5 μl of swelled affinity gel per tube was required to precipitate unbound enzyme following one hour of gentle shaking at room temperature. Choriomammotropin antibody was used at a titer of 1:1,000. The standard curve for the assay (FIG. 2) was developed to cover a range of 0–10 mg/l with maximum sensitivity between 1–4 mg/l.

EXAMPLE 2

Assay for Thyroxine (T-4)

A. Conjugate Preparation

As an initial step, a solution of beta-galactosidase in 0.05 M phosphate buffer was dialyzed to remove ammonium sulfate from the enzyme.

A solution was prepared at 0.2 mg/ml of m-maleimidobenzoyl-L-thyroxine methyl ester (MBTM) in the dialyzed enzyme solution, and this was subjected to further dialysis.

This dialyzed material was subjected to chromatography with Sephadex G-25, with the recovery of several aliquots. Tests on each of these aliquots with the substrate ONGP in BSA buffer at 0.8 mg/ml indicated those aliquots containing enzyme activity. The purpose of the chromatography was to eliminate the unbound MBTM from the enzyme-MBTM conjugate solution.

The $T_4$-enzyme conjugate was further purified by affinity chromatography using the same technique described in Ex. 1, to remove enzyme which had not bound to inhibitor.

B. Assay Procedure

To each of several glass test tubes (12 mm×75) was added 150 μl of buffer A, followed by the addition to each 0.1 ml of the T-4-enzyme conjugate, followed in turn by the addition to each of 0.1 ml of a different standard solution respectively. The standard solutions contained 0, 2.5, 5.0, 10 and 20 μg/dl of T-4 in 5% BSA solution.

After mixing, 0.1 ml of a 1:400 dilution of anti-T-4 antiserum was added to each test tube, followed by 0.4 ml of phosphate buffer. The assay mixture was then incubated for one hour.

A suspension of the same immobilized pseudo-substrate as in Ex. 1 then added to each tube. Each tube was then shaken for 60 minutes. The tubes were then centrifuged for 10 minutes at 2,000 rpm, and the supernatant liquids respectively were assayed for enzyme activity.

The observations were as follows:

TABLE 4

| Standardized Solution of $T_4$ Containing, in ug/dl | Observation, % $B/B_o$ |
|---|---|
| 0 | 100 |
| 2.5 | 87 |
| 5.0 | 72 |
| 10 | 63 |
| 20 | 53 |

These data were used to generate the standard curve shown in FIG. 2 of the drawings. It could then be used for individual sample assays in the same fashion as the HPL standard curve in Ex. 1.

EXAMPLE 3

Assay for Hepatitis B Surface Antigen

The hepatitis B surface antigen is a component of hepatitis B virus and its associated antibodies. It is a relatively large molecule. Its detection and determination are important because the transmission of the hepatitis virus via blood donors constitutes a significant public health risk.

One recent proposal for an assay for hepatitis antigens and their associated antibodies is discussed in U.S. Pat. No. 4,016,043. This assay is based on a competition reaction where one of the reactants is bonded to an insoluble carrier material.

Our procedure is different and parallels that used in Exs. 1 and 2 hereof and makes use of our novel separation technique. The assay procedure should involve adding the test sample, i.e., human serum or plasma, to a solution of a given amount of an antigen-enzyme conjugate. The given amount should be selected so that it is preferably at least 50% in excess over that required to react fully with a known quantity of antibody against hepatitis B surface antigen, which should also be added. As in Exs. 1 and 2, the conjugate reactant should be carefully purified, and a standard curve developed.

After incubation, passage of the resulting reaction mixture over the affinity gel, or admixture with it if granules or beads are used, will precipitate out conjugate that is not bound to antibody. After separation from the precipitate, a determination of enzyme activity on the liquid will produce a value that can be applied to the standard curve to provide an indication of the presence and concentration of the antigen in the serum.

EXAMPLE 4

Direct Assay for Antibodies Against Hepatitis B Surface Antigen in Human Serum or PLasma To check serum after vaccination, for example, a different assay procedure is needed than that of Exs. 1, 2 and 3. It makes use of our novel separation process.

In this procedure, for example, in the detection of antibodies against hepatitis B surface antigen, the serum or plasma sample will be suspected of containing antibody against hepatitis B surface virus. The conjugate employed should be a conjugate of (1), the antigen that is immunoreactant with this antibody, with (2), enzyme, preferably betagalactosidase. A standard curve should be prepared from a serum sample containing a given or known amount of antibodies against hepatitis B antigens using just these two reactants, i.e., the sample (containing the antibodies) and the antigen-enzyme conjugate. Once the standard curve has been constructed, it is used in the same fashion as in Ex. 1. However, in making the assay, the only reactants that are essential are: the unknown, containing antibody material; the antigen-enzyme conjugate, furnishing a given amount of antigenic activity, i.e., a given amount of immunochemical reactivity as to its binding partner, the antibody material in the unknown; the affinity gel; and whatever is needed to detect and/or determine enzyme activity in either the supernatant or in the precipitate on the affinity gel.

In this case, the immunochemical reactant activity in the conjugate should be selected always to be greater than that expected in the unknown. Then, the activity found in the supernatant should indicate, by differing from the original given amount, the amount of antibody material present in the unknown.

This simplified assay procedure may be used wherever the antibody material to be detected and/or determined is very specific, as is the case with the antibody for each of rubella virus, hepatitis B surface antigen, and gonorrhea.

EXAMPLE 5

Competitive Assays for More General Immunoglobulins

The assay technique for use in detecting immunoglobulins may be a simple variation on the assay procedures of Exs. 1 and 2. Thus, to detect and determine IgG, IgM, IgE, and IgA, the assay procedure of Ex. 1 should be modified.

The conjugate employed should be a conjugate of the particular immunoglobulin with enzyme. The receptor added to the incubated mixture of serum sample and conjugate should be antibody to the particular immunoglobulin to be detected. The affinity gel employed may be the same as in Ex. 1.

A standard curve must be prepared as in Ex. 1, but adjusted for appropriate standard solution concentrations. The standard curve may then be used in the same way as that in Ex. 1. Also, the procedural steps to be followed are essentially the same as those of Ex. 1. This provides a very sensitive assay.

General

The assay procedures of the present invention exhibit good separation, provide good sensitivity, and have unusual reliability for both small and large molecules, and for viruses as well. They can be applied to infectious disease detection and will be useful in providing and in developing new assays for parasites which will be important in developing countries.

Commercially the assay procedure will be made available through the manufacture and sale of assay kits with instructions, as well as through commercial laboratories.

Kit for Competitive Assay Procedures

In one such embodiment of the invention, the kit will be one for detecting the presence of ligand such as an antigen, hormone, steroid, or hapten, in a medium suspected of containing it. Such a kit will include all necessary supplies of the following components, preferably at concentrations and in amounts useful in carrying out the assay procedure, or easily dilutable to be such:

(1), ligand-enzyme conjugate, where the ligand is the same as or the immunochemical equivalent of that for which the assay procedure is to be conducted;

(2), receptor for the ligand, that is, an entity that can specifically bind to the ligand moiety of the conjugate and also to the ligand in the sample of the liquid on which the assay is to be conducted; and (3), immobilized, insoluble pseudo-substrate for said enzyme, to which the enzyme normally binds.

The receptor must be characterized by the ability, when bound to the ligand moiety of the conjugate, to inhibit the ability of the enzyme moiety of the conjugate to bind to the insoluble, immobilized pseudo-substrate.

The enzyme will preferably be selected from the group consisting of horse-radish peroxidase, alkaline phosphatase, beta-D-galactosidase, glucose oxidase, glucoamylase, carbonic anhydrase, acetylcholinesterase, lysozyme, malate dehydrogenase, and glucose-6-phosphate dehydrogenase. The most preferred enzyme is beta-galactosidase. Generally, to form the enzyme-ligand conjugate, the enzyme will be bound to the ligand by a cross-linker. When the enzyme is beta-galactosidase, the immobilized pseudo-substrate will preferably be formed from beta-D-galactosylamine that is covalently coupled to insoluble particles of a carrier substance, preferably agarose, that is inert to the assay procedure, through a bridge that contains at least six carbons.

In one preferred embodiment, where the assay is for HPL, the enzyme is beta-galactosidase; the conjugate is HPL coupled to the enzyme by MBS as in Ex. 1, in as close to a 12 to 1 molar ratio as is feasible; the pseudo-substrate is beta-D-galactosylamine, and the receptor is an anti-choriomammotropin antibody. To be complete, such a kit should also include enzyme substrate, and printed instructions for carrying out the assay, as outlined above and as described in detail in Ex. 1. In many cases, these instructions will include one or more standard curves. For this preferred embodiment, the preferred enzyme substrate is ONGP.

For a kit to detect the presence of thyroxine, preferably the enzyme is beta-galactosidase, the conjugate consists of T-4 coupled to the enzyme as in Ex. 2, the pseudo-substrate is beta-D-galactosylamine, and the receptor is an anti-thyroxine antibody. The preferred enzyme substrate is again ONGP.

The kit can be modified readily for use in the detection of general antibodies, such as, for example, IgG, IgM, IgE, or IgA. In this case the general antibody is the ligand, and the receptor is antibody to the general antibody, that is, an antibody to the particular immunoglobulin that is to be detected.

Kit for Direct Assay Procedures

In another embodiment, the kit may be designed for carrying out an assay procedure to detect the presence, if any, of a specific antibody in a medium suspected of containing it.

Such a kit will include supplies of the following components, at concentrations and in amounts useful in carrying out the assay procedure:

(1), a conjugate of an enzyme with the antigen or immunochemical equivalent thereof for the suspected specific antibody;

(2), insoluble, immobilized pseudo-substrate for said enzyme, to which said enzyme normally binds, and (3), enzyme substrate that generates a color reaction when exposed to the enzyme or the enzyme moiety of the conjugate.

In this case, the antibody is characterized by the ability, when bound to the antigen moiety of the antigen-enzyme conjugate, to inhibit the ability of the enzyme moiety of the conjugate to bind to the insoluble, immobilized pseudo-substrate. The reading of the assay result is made on liquid separated from the immobilized pseudo-substrate, preferably with an indicator-type of substrate for the enzyme, which may also be a part of the kit. Once again, ONGP is a preferred such substrate.

Among the specific antibodies that may be detected in this way are those for rubella virus, hepatitis B surface antigen, and gonorrhea antigen.

To be complete, this kit also must include printed instructions for carrying out the direct assay procedures, as outlined above and as described in detail in Ex. 4. These instructions preferably will include one or more standard curves.

Conclusion

The unknown typically is present in tremendous excess over that needed for a complete immunochemical reaction. Generally, the greater the excess, the more sensitive the assay. For a qualitative assay, it is possible for the conjugate to be in any relation to the unknown, preferably much less than is required for a complete immunochemical reaction. For a quantitative assay, the immunochemically reactive moiety of the conjugate must be present in at least an equal and preferably a greater amount than is needed for a complete immunochemical reaction with the receptor. The affinity gel is preferably always present to excess over that needed for completely reaction with the enzyme.

In preparing the conjugate, the use of the proper molar ratio, and the purification of the conjugate by affinity chromatography as illustrated in Ex. 1, are very important to minimize the "noise" level of the assay.

While the invention has been described in connection with specific embodiments thereof, it will be understood that it is capable of further modifications, and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as fall within the scope of the appended claims.

What is claimed is:

1. A process for separating a dissolved unbound ligand-enzyme conjugate from the same conjugate bound to a receptor for the ligand moiety and dissolved in the same solution, comprising:
contacting (i) an aqueous solution containing both an unbound ligand-enzyme conjugate and the same conjugate bound through its ligand moiety to a receptor that binds specifically to the ligand, with (ii) an insoluble immobilized pseudo-substrate for the enzyme moiety of said conjugate, said receptor and said pseudo-substrate being so selected that
(a) the enzyme moiety of the ligand-enzyme conjugate binds to the immobilized pseudo-substrate, and
(b) the receptor, when bound to the ligand moiety of the ligand-enzyme conjugate, inhibits the binding of the enzyme moiety of the bound conjugate to the immobilized pseudo-substrate,
whereby the unbound ligand-enzyme conjugate is immobilized to the insoluble immobilized pseudo-substrate and removed from the solution while the receptor-bound conjugate remains in solution.

2. The process of claim 1 wherein the ligand is an antigen, hapten, steroid, or hormone, and the receptor is an antibody thereto.

3. The process of claim 2 wherein the ligand is choriomammotropin.

4. The process of claim 3 wherein the enzyme is beta-galactosidase and the pseudo-substrate is beta-D-galacto-sylamine that is immobilized on insoluble granules of an organic carrier material.

5. The process of claim 2 wherein the ligand is thyroxine.

6. The process of claim 1 wherein the ligand is a specific antibody.

7. The process of claim 6 wherein the ligand is the antibody to hepatitis B surface antigen.

8. The process of claim 6 wherein the ligand is the antibody to rubella virus.

9. The process of claim 6 wherein the ligand is the antibody to gonorrhea antigen.

10. The process of claim 1 wherein the ligand is a general antibody and the receptor is an antibody to the antibody.

11. The process of claim 10 wherein the ligand is an antiserum selected from the group consisting of IgG, IgM, IgE, and IgA.

12. The process of claims 1, 2, 3 or 4, wherein the enzyme is beta-galactosidase and the pseudo-substrate is beta-D-galactosylamine immobilized to insoluble granules of an organic carrier material through a bridge containing at least six carbons.

13. The process of claim 1 wherein the enzyme is selected from the group consisting of horse-radish peroxidase, alkaline phosphatase, beta-D-galactosidase, glucose oxidase, glucoamylase, carbonic anhydrase, acetylcholinesterase, lysozyme, malate dehydrogenase, and glucose-6-phosphate dehydrogenase.

14. The process of claim 1 wherein said processed solution from the separation step is essentially free of unbound ligand-enzyme conjugate.

15. The process of claim 14 wherein said aqueous liquid medium and said processed solution also contain free ligand, from a sample suspected of containing it.

16. The process of claim 15 wherein the ligand of the conjugate and the ligand from the sample are the same material.

17. The process of claim 15 wherein the ligand of the conjugate and the ligand from the sample are different materials but the receptor binds specifically to each.

18. An assay procedure for detecting or determining a dissolved ligand in a medium suspected of containing it, comprising:
combining in an aqueous liquid vehicle, to form a mixture:
(1) said medium,
(2) a given amount of a soluble conjugate of an enzyme with the same ligand or its immunochemical equivalent as the ligand to be detected, and
(3) a given amount of a receptor capable of specifically binding to both the ligand to be detected and the ligand moiety of the conjugate, the relative amounts of conjugate and of receptor being such that there is an excess of the conjugate present over that necessary to bind with the receptor,
contacting said mixture with an insoluble immobilized pseudo-substrate for the enzyme moiety of said conjugate whereby
said receptor bound to the ligand moiety of said conjugate inhibits said conjugate from binding to said immobilized pseudo-substrate;
separating said insoluble immobilized pseudo-substrate having bound thereto, through the enzyme moiety of the conjugate, unbound conjugate from the liquid, and
detecting the enzyme activity of either said liquid or said separated pseudo-substrate as an indicator of the presence or quantity of the ligand in said original medium.

19. The procedure of claim 18 wherein the amount of immobilized pseudo-substrate is at least sufficient to bind all of the given amount of conjugate added, and the mixture is incubated before and after addition of immobilized pseudo-substrate.

20. The procedure of claims 18 or 19 wherein the relative amounts of the components of said mixture are such that there is always excess ligand reactivity present in the mixture.

21. The procedure of claim 20 wherein the ligand is a physiologically active substance present in said medium in a physiological effective concentration.

22. The procedure of claim 21 wherein said ligand is an antigen, a hapten, a steroid or a hormone.

23. The procedure of claim 21 wherein the enzyme is beta-galactosidase and the pseudo-substrate is beta-D-galactosylamine immobilized on insoluble granules of an organic substance, inert in the assay procedure, through a bridge containing at least six carbon atoms.

24. The procedure of claim 23 wherein the enzyme activity in said separated liquid is detected by adding to said liquid, as an enzyme substrate, o-nitrophenyl-beta-D-galactopyranoside.

25. The procedure of claim 23 wherein each said ligand is choriomammotropin, the receptor is anti-choriomammotropin, and the molar ratio in the conjugate of ligand to enzyme is in the range from about 8 to 1 to about 12 to 1.

26. The assay procedure of claim 21 wherein the ligand in said medium is a general antibody selected from the group consisting of IgG, IgM, IgE, and IgA.

27. The procedure of claim 20 wherein the ligand is thyroxine and the receptor is anti-thyroxine.

28. The assay procedure of claim 20 wherein the enzyme is selected from the group consisting of horseradish peroxidase, alkaline phosphatase, beta-galactosidase, glucose oxidase, glucoamylase, carbonic anhydrase, acetylcholinesterase, lysozyme, malate dehydrogenase, and glucose-6-phosphate dehydrogenase.

29. The assay procedure of claim 20 wherein the amount of said medium employed is selected, based on an expected content of the ligand, in said medium so that there is a competitive reaction, for the receptor, between the ligand in the medium and the ligand moiety of the conjugate, and wherein a standard curve is employed that correlates detected enzyme activity in said separated liquid with ligand concentration in said original medium.

30. The assay procedure of claim 20 wherein the ligand is a specific antibody, the soluble conjugate is formed from an enzyme and a ligand which is a specific binding partner for said specific antibody and the receptor is omitted.

31. The assay procedure of claim 30 wherein said ligand is hepatitis B surface antigen or rubella virus.

32. The assay procedure of claims 30, or 31 wherein the enzyme is beta-galactosidase and the pseudosubstrate is beta-D-galactosylamine immobilized on insoluble granules of an organic substance, which is inert in the assay procedure, through a bridge containing at least six carbon atoms.

33. The assay procedure of claim 32 wherein the enzyme activity in said separated liquid is detected by adding to the liquid, as an enzyme substrate, O-nitrophenyl-beta-D-galactopyranoside.

34. The assay procedure of claims 30 wherein the enzyme is selected from the group consisting of horseradish peroxidase, alkaline phosphatase, beta-galactosidase, glucose oxidase, glucoamylase, carbonic anhydrase, acetylcholinesterase, lysozyme, malate dehydrogenase, and glucose6-phosphate dehydrogenase.

35. An assay procedure according to claim 20 wherein the ligand is a general antibody.

36. An assay procedure according to claim 35 wherein the ligand is a general antibody and the receptor is an antiserum which is a specific binding partner for said general antibody.

37. The assay procedure of claim 36 wherein said general antibody is selected from the group consisting of $I_gG$, $I_gM$, $I_gE$, and $I_gA$.

38. The assay procedure of claim 37 wherein the enzyme of said conjugate is beta-galactosidase and the pseudosubstrate is beta-D-galactosylamine that is immobilized to insoluble granules of an organic substance that is inert in the assay procedure, through a bridge containing at least six carbon atoms.

39. The procedure of claim 38 wherein the enzyme activity in said separated liquid is detected by adding to the liquid, as an enzyme substrate, O-nitrophenyl-beta-D-galactopyranoside.

40. The assay procedure of claim 36 wherein the enzyme is selected from the group consisting of horseradish peroxidase, alkaline phosphatase, beta-galactosidase, glucose oxidase, glucoamylase, carbonic anhydrase, acetyl-cholinesterase, lysozyme, malate dehydrogenase, and glucose-6-phosphate dehydrogenase.

41. A kit for use in carrying out the assay procedure of claim 20 comprising a conjugate of an enzyme with an immunochemically reactive material;
an insoluble, immobilized pseudo-substrate for said enzyme; and
a chemical means for detecting the presence of said conjugate, wherein the conjugate, insoluble pseudo-substrate and means are present in relative amounts for the detection of the ligand.

42. The kit of claim 41 wherein the detecting means comprises means for detecting or determining enzyme activity through a color producing reaction in a liquid phase.

43. The kit of claim 42 wherein the enzyme in the conjugate is beta-galactosidase and the immobilized pseudo-substrate comprises beta-D-galactosylamine coupled, through a bridge containing at least six carbon atoms, to insoluble particles of a carrier substance inert to the assay procedure.

44. A kit according to claim 43 that also includes, as an enzyme substrate, o-nitrophenyl-beta-D-galactopyranside.

45. A kit according to claim 41 wherein an effective amount of a receptor is included, said receptor being a specific binding partner for the ligand to be detected and for the immunochemically reactive moiety of the conjugate.

46. A kit according to claim 45 wherein said immunochemically reactive material is a ligand selected from the group consisting of an antigen, hapten, steroid or hormone.

47. The kit according to claim 45 wherein said enzyme is selected from the group consisting of horse-radish peroxidase, alkaline phosphatase, beta-galactosidase, glucose oxidase, glucoamylase, carbonic anhydrase, acetylcholinesterase, lysozyme, malate dehydrogenase, and glucose-6-phosphate dehydrogenase.

48. The kit according to claim 45 wherein the ligand is choriomammotropin, the enzyme is beta-galactosidase, the pseudo-substrate is beta-D-galactosylamine, and the receptor is an anti-choriomammotropin antibody.

49. A kit according to claim 45 wherein the ligand is thyroxine, the enzyme is beta-galactosidase, the pseudo-substrate is beta-D-galactosylamine that is coupled to insoluble particles of a carrier substance that is inert to the assay procedure, through a bridge that contains at least six carbons atoms and the receptor is an anti-thyroxine antibody.

50. The kit of claim 49 including, as a substrate and indicator for enzyme activity, o-nitrophenyl-beta-D-galactopyranoside.

51. A kit according to claim 45 wherein the immunochemically reactive material is a general antibody.

52. A kit according to claim 51 wherein the general antibody is selected from the group consisting of IgG, IgM, IgE, and IgA, and wherein the receptor is an antibody to the particular immunoglobulin that is to be detected.

* * * * *

UNITED STATES PATENT AND TRADEMARK OFFICE
CERTIFICATE OF CORRECTION

PATENT NO. : 4,323,647
DATED : April 6, 1982
INVENTOR(S) : NOBUO MONJI and ALBERT CASTRO It is certified that error appears in the above-identified patent and that said Letters Patent is hereby corrected as shown below:

Col. 3, l. 46 - "competitions" should be -- competition --
Col. 5, l. 31 "class" should be -- classes --
      l. 38 "side" should be -- site --
      l. 41 "use" should be -- used --
Col. 9, l. 5 "bending" should be -- binding --
Col. 13, l. 17 "with be selected" should be -- will be selected --
Col. 14, l. 63 "liquid" should be --ligand --
Col. 15, l. 21, "liquid" should be - ligands --
Col. 18, ll. 56-57 "interest" should be -- inherent --

Col. 22, l. 28, "1969" should be -- 1967 --
Col. 32, l. 9 "completely" should be -- complete --

Signed and Sealed this

Ninth Day of August 1983

[SEAL]

Attest:

GERALD J. MOSSINGHOFF

Attesting Officer    Commissioner of Patents and Trademarks